(12) United States Patent
Zerbe et al.

(10) Patent No.: US 10,982,232 B2
(45) Date of Patent: Apr. 20, 2021

(54) DITERPENE SYNTHASES AND THEIR USE FOR PRODUCTION OF DITERPENES

(71) Applicant: The Regents of the University of California, Oakland, CA (US)

(72) Inventors: Philipp Zerbe, Oakland, CA (US); Sibongile Mafu, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/320,362

(22) PCT Filed: Jul. 25, 2017

(86) PCT No.: PCT/US2017/043786
§ 371 (c)(1),
(2) Date: Jan. 24, 2019

(87) PCT Pub. No.: WO2018/022654
PCT Pub. Date: Feb. 1, 2018

(65) Prior Publication Data
US 2019/0241912 A1 Aug. 8, 2019

Related U.S. Application Data

(60) Provisional application No. 62/367,264, filed on Jul. 27, 2016.

(51) Int. Cl.
| | | |
|---|---|---|
| C12N 9/88 | (2006.01) |
| C12P 5/00 | (2006.01) |
| A61K 31/015 | (2006.01) |
| C07C 13/47 | (2006.01) |
| C12P 17/06 | (2006.01) |
| C12N 15/52 | (2006.01) |
| C12N 15/70 | (2006.01) |
| C12N 15/81 | (2006.01) |

(52) U.S. Cl.
CPC .............. *C12P 5/00* (2013.01); *A61K 31/015* (2013.01); *C07C 13/47* (2013.01); *C12N 9/88* (2013.01); *C12N 15/52* (2013.01); *C12N 15/70* (2013.01); *C12N 15/81* (2013.01); *C12P 5/007* (2013.01); *C12P 17/06* (2013.01); *C12Y 402/03* (2013.01); *C07C 2602/26* (2017.05)

(58) Field of Classification Search
CPC ......................................................... C12N 9/88
USPC ........................................................... 435/232
See application file for complete search history.

(56) References Cited

U.S. PATENT DOCUMENTS 6,887,895 B2    5/2005   Yue et al.
2014/0371311 A1  12/2014  Oh et al.

FOREIGN PATENT DOCUMENTS

WO    2009/044336 A9    4/2009
WO    2013/110673 A1    8/2013

OTHER PUBLICATIONS

Campbell et al, Nuclear ribosomal DNA internal transcribed spacer 1 (ITS1) in Picea (Pinaceae): sequence divergence and structure. Molecular Phylogenetics and Evolution 35 (2005) 165-185.*
Hall et al, Evolution of Conifer Diterpene Synthases: Diterpene Resin Acid Biosynthesis in Lodgepole Pine and Jack Pine Involves Monofunctional and Bifunctional Diterpene Synthases Plant Physiology, Feb. 2013, vol. 161, pp. 600-616.*
NCBI Acc#KU685114.1 Palazzo et al, Discovery and mechanistic analysis of a diterpene synthase of Pseudolarix amabilis with potential chemotherapeutic applications (2017).*
International Search Report in PCT/US2017/043786, dated Nov. 9, 2017.
Byun-McKay, et al. "Wound-induced terpene synthase gene expression in Sitka spruce that exhibit resistance or susceptibility to attack by the white pine weevil." Plant physiology 140, No. 3 (2006): 1009-1021.
Keeling, et al. "Transcriptome mining, functional characterization, and phylogeny of a large terpene synthase gene family in spruce (*Picea* spp.)." BMC plant biology 11, No. 1 (2011): 43.
Mafu, et al. "Biosynthesis of the microtubule-destabilizing diterpene pseudolaric acid B from golden larch involves an unusual diterpene synthase." Proceedings of the National Academy of Sciences 114, No. 5 (2017): 974-979.
Zerbe, et al. "Plant diterpene synthases: exploring modularity and metabolic diversity for bioengineering." Trends in biotechnology 33, No. 7 (2015): 419-428.

* cited by examiner

*Primary Examiner* — Sheridan Swope
(74) *Attorney, Agent, or Firm* — Kilpatrick Townsend and Stockton LLP

(57) ABSTRACT

Diterpene synthases and methods of their use are described herein.

20 Claims, 14 Drawing Sheets

Specification includes a Sequence Listing.

Structure and stereochemistry of sibongilene

SEQUENCE LISTING

<160> NUMBER OF SEQ ID NOS: 43

<210> SEQ ID NO 1
<211> LENGTH: 846
<212> TYPE: PRT
<213> ORGANISM: Psuedolarix amabilis

<400> SEQUENCE: 1

Met Ser Arg Phe Thr Ser Ala Thr His Gly Leu Asn Leu Ser Ile Lys
1               5                   10                  15

Met Pro Ile Ser Val Ser Gln Val Pro Ser Ile Arg Ser Asn Thr Ser
            20                  25                  30

Lys Tyr Glu Leu Gln Lys Leu Arg Ser Thr Gly Arg Ser Val Leu Gln
        35                  40                  45

Thr Arg Arg Gln Leu Ala Ile Ile Asn Met Thr Lys Arg Ser Glu Ala
    50                  55                  60

Asp Asp Asn Asp Gly Val Glu Arg Arg Lys Gly Val Phe His Pro Asn
65                  70                  75                  80

Leu Trp Asp Asp Gly Phe Ile Gln Ser Leu Ser Thr Val Tyr His Glu
                85                  90                  95

Gln Ala Ser Tyr Arg Glu Arg Ala Glu Arg Leu Ile Gly Glu Val Lys
            100                 105                 110

Ala Val Phe Asp Ser Ile Ser Met Gly Asp Gly Asp Gln Phe Ile Ser
        115                 120                 125

Pro Ser Ala Tyr Asp Thr Ala Trp Val Ala Arg Val Pro Ala Ile Asp
    130                 135                 140

```
Gly Ser Ser Arg Pro Gln Phe Pro Gln Ala Ile Asp Trp Ile Leu Leu
145                 150                 155                 160

Asn Gln Gln Gln Asp Gly Ser Trp Gly Ser Gln Ser His Leu Ser Leu
            165                 170                 175

Thr His Arg Leu Thr Asp Thr Leu Ala Cys Val Ile Ala Leu Ala Ser
        180                 185                 190

Trp Lys Ile Glu Ser Val Gln Ile Asp Glu Gly Leu Asp Phe Ile Thr
    195                 200                 205

Arg Gly Val Glu Lys Leu Gln Ser Glu Ser Val Pro Ala Glu Phe Glu
210                 215                 220

Ile Ile Phe Ala Glu Leu Leu Asn Gln Ala Lys Ser Leu Gln Leu Ser
225                 230                 235                 240

Leu Pro Tyr Glu His Ser Cys Leu Gln Ser Leu Trp Arg Lys Gln Glu
                245                 250                 255

Pro Ile Leu Ala Asn Gly Leu Met Asp Ser Val Ala Lys Arg Ser Leu
            260                 265                 270

Ser Ser Leu Glu Glu Met Gln Asp His Arg Met Asn Thr Asp Ser Asp
        275                 280                 285

Gly Thr Met His Val Glu Ser Phe Leu Ser Ser Pro Ala Val Ala Ala
290                 295                 300

Arg Val Leu Met Arg Thr Gly Asn Pro Ile Cys Leu Ala Tyr Leu Asn
305                 310                 315                 320

Asn Val Leu Asn Lys Phe Gly Asp Tyr Val Pro Gly Met Tyr Pro Val
                325                 330                 335

Asp Leu Phe Gln Arg Leu Trp Met Val Asp Asn Val Glu Arg Leu Gly
            340                 345                 350

Ile Asp Arg His Phe Lys Lys Glu Ile Gln Val Thr Leu Asp Tyr Val
        355                 360                 365

Tyr Ser Tyr Trp Asn Gly Lys Gly Ile Gly Cys Gly Arg Asp Ser Leu
370                 375                 380

Ser Pro Asp Leu Asn Ser Thr Ser Leu Gly Phe Arg Thr Leu Arg Leu
385                 390                 395                 400

His Gly Tyr Asn Val Ser Ala Asp Val Leu Glu His Phe Lys Asp Arg
                405                 410                 415

Asp Gly Lys Phe Val Cys Ser Ser Asn Pro Thr Val Gly Glu Ile Arg
            420                 425                 430

Ser Val Leu Asn Leu Tyr Arg Ala Ser Leu Leu Ala Phe Pro Gly Glu
        435                 440                 445

Lys Val Met Glu Glu Ala Glu Thr Phe Ala Arg Arg Tyr Leu Glu Glu
450                 455                 460

Ile Val Gln Lys Ile Pro Pro Ser Lys Phe Ser Arg Glu Ile Glu Tyr
465                 470                 475                 480

Val Leu Glu Phe Gly Trp Gln Ser Thr Val Pro Arg Trp Glu Ala Arg
                485                 490                 495

Ser Tyr Ile Asp Phe His Gly Leu Asp Thr Tyr Ser Pro Trp Thr Ile
            500                 505                 510

Tyr Glu Met Ala Ser Glu Lys Phe Leu Glu Leu Ala Lys Leu Glu Phe
        515                 520                 525

Asn Ile Phe Asn Ser Leu Gln His Thr Glu Leu Gln Tyr Leu Ser Arg
530                 535                 540

Trp Trp Asn Asp Ser Gly Met Ser Gln Met Arg Phe Thr Arg His Arg
545                 550                 555                 560
```

```
Asn Val Glu Tyr Tyr Thr Met Ala Ser Cys Ile Ala Met Glu Pro Ser
                565                 570                 575

Gln Ser Ala Phe Arg Ile Gly Phe Thr Lys Leu Cys Gly Ile Ala Thr
            580                 585                 590

Cys Ile Asp Asp Ile Tyr Asp Thr Tyr Gly Thr Ile Asp Glu Leu Lys
        595                 600                 605

Leu Phe Arg Glu Ala Val Lys Arg Trp Asp Pro Ser Ala Ile Glu Ser
610                 615                 620

Leu Pro Glu Tyr Met Lys Ser Val Tyr Met Val Leu Tyr Glu Leu Val
625                 630                 635                 640

Asn Glu Met Ala Gln Asp Thr Glu Arg Thr Gln Gly Arg Asp Thr Leu
                645                 650                 655

Asp Tyr Ala Arg Asn Ala Trp Glu Ala Ile Ile Asp Ala His Leu Val
            660                 665                 670

Glu Ala Glu Trp Ile Ala Ser Gly His Ile Pro Thr Phe Glu Glu Tyr
        675                 680                 685

Leu Glu Asn Ser Lys Val Thr Ser Gly Leu His Ile Ala Ile Leu Pro
690                 695                 700

Ile Leu Thr Leu Asp Val Pro Leu Pro Asp Gln Leu Pro Leu Gln Glu
705                 710                 715                 720

Ile Asp Thr Leu Ser Arg Phe His His Leu Ala Ser Thr Ile Gly Arg
                725                 730                 735

Leu Ser Gly Asp Met Asn Ala Tyr Lys Ile Asp Leu Ala His Gly Glu
            740                 745                 750

Glu Ser Ser Cys Ile Ser Cys Tyr Met Lys Asp Asn Pro Gly Thr Thr
        755                 760                 765

Glu Gly Asp Ala His Asn Tyr Ala Asn Val Thr Ile Ser Tyr Leu Met
770                 775                 780

Lys Glu Leu Asn Leu Glu Leu Met Gly Gln His Asn Arg Val Ser Phe
785                 790                 795                 800

Leu Arg Thr Ser Lys Lys Pro Ala Phe Asp Ile Tyr Arg Ala Ser Asn
                805                 810                 815

Tyr Met Tyr Lys Tyr Arg Asp Gly Tyr Thr Ile Ala Asp Lys Glu Thr
            820                 825                 830

Lys Asn Leu Val Met Arg Thr Leu Val Gln Ala Val Ser Leu
        835                 840                 845

<210> SEQ ID NO 2
<211> LENGTH: 2445
<212> TYPE: DNA
<213> ORGANISM: Psuedolarix amabilis

<400> SEQUENCE: 2
atggctggcg tttctgttga atcaaaagtt ccagtttgg tttgtaattt atcgagtacc      60
agcggcttga ttcgaagaac ggccaatcct catcctaatg tctggggtta tgactttgtt     120
cattctctca atcaccttta tactgattct agttacagag aacgggcaga tgcccttgtt     180
gtcgagatta aagccatgct gaatgcagcc attgcaggag atggagaatc aacgattact     240
ccatctgctt atgacacagc atgggtagcc agggtgcccg ccattgatgg ctctgctcgc     300
ccgcagtttc cccaaacagt tgattggatt ttgaaaaacc agttaaaaga tggttcatgg     360
gggattgagt cccactttct gctgtccgat cgccttcttg ctactctttc ttgtgttatt     420
gctcttttta aatggaacgt tggggatctg caagtaaagc agggaattga attcataaag     480
agcaatctgg aactcgtaaa ggatgaaagc gatcaagaca gcttggtaac agattttgag     540
```

| | |
|---|---|
| atcatcttcc cttccctgtt aagagaagct caatctctga gccttgaact tccctacgac | 600 |
| ctgccttata tacatctgtt gcagactaaa cggcaggaaa gattagcaaa agtttccagg | 660 |
| gaagaaattt acaccgttcc ttcgccactg ttgtattctc tggaaggaat acaagatata | 720 |
| gttgagtggg atcgaataat ggatgttcaa ggccaggatg ggtcattctt aagctcgcct | 780 |
| gcttccactg cctgcgtttt tatagatgtg aaatgccttg aattcttgaa caatgtgatg | 840 |
| atgaagttgg gaaattttgt tccctgcctg tatcctgtgg atctgctaga gcgcctgttg | 900 |
| atcgtggata acattgaacg ccttggaatt tatagacact ttgaaaagga aatcaacgaa | 960 |
| gctctcgatt atgtttacag gcattggaac gaaagaggaa ttgggtgggg cacacggaat | 1020 |
| cccatagcag atcttgagac cactgctttg ggatttctat tgcttcggct gcatcggtac | 1080 |
| aatgtatctc cagccgtttt cgacaacttc aaagattcca atgggcaatt cttttgctcg | 1140 |
| accggtcaac tcaacaaaga tgtagcaagc atgttgagcc tttatagagc ttcccagctt | 1200 |
| gcatttcccg gagaagacat tttggacgaa gctaaaagct tcactactaa atatttgaga | 1260 |
| gaagctcttg agaaaagtga gacttccagt gcatggaaca caaacaaaa tctgagccaa | 1320 |
| gagatcaaat acgcgctgaa gacttcctgg catgccagtg tcgccagagt ggaagcaaag | 1380 |
| agatactgtc aagtgtatcg cccagattat gcacgcctag ccaaaagcgt ttacaggctg | 1440 |
| ccttacgtga acaatgaaaa gttcttagag ctgggaaaat tagatttcaa cattatccag | 1500 |
| gccatccacc aagaagaaat gaagactgtt accagctggt ttagagattc gggtttgcct | 1560 |
| ttattcacct tcgctcggga aaggccactg gaattctact tcttagtagc cactgggacg | 1620 |
| tatgagcctc aatatgccaa atgcagattc ctctttacaa aagttgcatg cttgcagact | 1680 |
| gttttggacg atatgtatga cacttatgga accctagatg aattgaagct attcactgag | 1740 |
| gctgtaagaa gatgggacct ctcttttaca gaaaaccttc cagactacat gaaactatgt | 1800 |
| tacaaaatct attatgacat agttcacgaa gtggcttggg aggcagagaa ggaacagggg | 1860 |
| cgtgaattgg ttagcttttt cagaaaggga tgggaggatt atcttctggg ttactatgaa | 1920 |
| gaagctgaat ggctggctag tgagtatgtg ccgagcttgg acgagtacat aaagaatgga | 1980 |
| atcacgtcca ttggccagcg tatacttctg ctgagtggag tgttgataat ggatgggcag | 2040 |
| ctactttccc aagaagcatt ggagaaagta gattatccag gaaggcgtgt tctcacagag | 2100 |
| cttaacagcc tcatttcccg cctggcagac gacacaaaga cctacaaagc tgagaaggct | 2160 |
| cgtggagaat tggcatccag catagaatgt tacatgaaag accatcctga atgtacagag | 2220 |
| gaagaggctc tcgctcacat ctatagcatt ctggaacccg cggtgaagga actgacacgg | 2280 |
| gagtttctga gcccgacga cgtcccgttc gcgtgcaaga aaatgctttt cgaagagacg | 2340 |
| agagtgacaa tggtgatatt taaggatgga gatggtttcg gcgtttccaa attagaagtc | 2400 |
| aaagatcata tcaaagagag tctaattgat ccgctcccac tttaa | 2445 |

<210> SEQ ID NO 3
<211> LENGTH: 818
<212> TYPE: PRT
<213> ORGANISM: Psuedolarix amabilis

<400> SEQUENCE: 3

```
Ser Asn Thr Ser Lys Tyr Glu Leu Gln Lys Leu Arg Ser Thr Gly Arg
1               5                   10                  15

Ser Val Leu Gln Thr Arg Arg Gln Leu Ala Ile Ile Asn Met Thr Lys
            20                  25                  30
```

-continued

```
Arg Ser Glu Ala Asp Asp Asn Asp Gly Val Glu Arg Lys Gly Val
         35                  40                  45
Phe His Pro Asn Leu Trp Asp Asp Gly Phe Ile Gln Ser Leu Ser Thr
 50                  55                  60
Val Tyr His Glu Gln Ala Ser Tyr Arg Glu Arg Ala Glu Arg Leu Ile
 65                  70                  75                  80
Gly Glu Val Lys Ala Val Phe Asp Ser Ile Ser Met Gly Asp Gly Asp
                 85                  90                  95
Gln Phe Ile Ser Pro Ser Ala Tyr Asp Thr Ala Trp Val Ala Arg Val
                100                 105                 110
Pro Ala Ile Asp Gly Ser Ser Arg Pro Gln Phe Pro Gln Ala Ile Asp
                115                 120                 125
Trp Ile Leu Leu Asn Gln Gln Gln Asp Gly Ser Trp Gly Ser Gln Ser
 130                 135                 140
His Leu Ser Leu Thr His Arg Leu Thr Asp Thr Leu Ala Cys Val Ile
 145                 150                 155                 160
Ala Leu Ala Ser Trp Lys Ile Glu Ser Val Gln Ile Asp Glu Gly Leu
                165                 170                 175
Asp Phe Ile Thr Arg Gly Val Glu Lys Leu Gln Ser Glu Ser Val Pro
                180                 185                 190
Ala Glu Phe Glu Ile Ile Phe Ala Glu Leu Leu Asn Gln Ala Lys Ser
                195                 200                 205
Leu Gln Leu Ser Leu Pro Tyr Glu His Ser Cys Leu Gln Ser Leu Trp
 210                 215                 220
Arg Lys Gln Glu Pro Ile Leu Ala Asn Gly Leu Met Asp Ser Val Ala
225                 230                 235                 240
Lys Arg Ser Leu Ser Ser Leu Glu Glu Met Gln Asp His Arg Met Asn
                245                 250                 255
Thr Asp Ser Asp Gly Thr Met His Val Glu Ser Phe Leu Ser Ser Pro
                260                 265                 270
Ala Val Ala Ala Arg Val Leu Met Arg Thr Gly Asn Pro Ile Cys Leu
                275                 280                 285
Ala Tyr Leu Asn Asn Val Leu Asn Lys Phe Gly Asp Tyr Val Pro Gly
 290                 295                 300
Met Tyr Pro Val Asp Leu Phe Gln Arg Leu Trp Met Val Asp Asn Val
305                 310                 315                 320
Glu Arg Leu Gly Ile Asp Arg His Phe Lys Lys Glu Ile Gln Val Thr
                325                 330                 335
Leu Asp Tyr Val Tyr Ser Tyr Trp Asn Gly Lys Gly Ile Gly Cys Gly
                340                 345                 350
Arg Asp Ser Leu Ser Pro Asp Leu Asn Ser Thr Ser Leu Gly Phe Arg
                355                 360                 365
Thr Leu Arg Leu His Gly Tyr Asn Val Ser Ala Asp Val Leu Glu His
 370                 375                 380
Phe Lys Asp Arg Asp Gly Lys Phe Val Cys Ser Ser Asn Pro Thr Val
385                 390                 395                 400
Gly Glu Ile Arg Ser Val Leu Asn Leu Tyr Arg Ala Ser Leu Leu Ala
                405                 410                 415
Phe Pro Gly Glu Lys Val Met Glu Glu Ala Glu Thr Phe Ala Arg Arg
                420                 425                 430
Tyr Leu Glu Glu Ile Val Gln Lys Ile Pro Pro Ser Lys Phe Ser Arg
                435                 440                 445
Glu Ile Glu Tyr Val Leu Glu Phe Gly Trp Gln Ser Thr Val Pro Arg
```

```
                450             455             460
Trp Glu Ala Arg Ser Tyr Ile Asp Phe His Gly Leu Asp Thr Tyr Ser
465                 470                 475                 480

Pro Trp Thr Ile Tyr Glu Met Ala Ser Glu Lys Phe Leu Glu Leu Ala
                485                 490                 495

Lys Leu Glu Phe Asn Ile Phe Asn Ser Leu Gln His Thr Glu Leu Gln
                    500                 505                 510

Tyr Leu Ser Arg Trp Trp Asn Asp Ser Gly Met Ser Gln Met Arg Phe
                515                 520                 525

Thr Arg His Arg Asn Val Glu Tyr Tyr Thr Met Ala Ser Cys Ile Ala
            530                 535                 540

Met Glu Pro Ser Gln Ser Ala Phe Arg Ile Gly Phe Thr Lys Leu Cys
545                 550                 555                 560

Gly Ile Ala Thr Cys Ile Asp Asp Ile Tyr Asp Thr Tyr Gly Thr Ile
                    565                 570                 575

Asp Glu Leu Lys Leu Phe Arg Glu Ala Val Lys Arg Trp Asp Pro Ser
                580                 585                 590

Ala Ile Glu Ser Leu Pro Glu Tyr Met Lys Ser Val Tyr Met Val Leu
                595                 600                 605

Tyr Glu Leu Val Asn Glu Met Ala Gln Asp Thr Glu Arg Thr Gln Gly
                610                 615                 620

Arg Asp Thr Leu Asp Tyr Ala Arg Asn Ala Trp Glu Ala Ile Ile Asp
625                 630                 635                 640

Ala His Leu Val Glu Ala Glu Trp Ile Ala Ser Gly His Ile Pro Thr
                    645                 650                 655

Phe Glu Glu Tyr Leu Glu Asn Ser Lys Val Thr Ser Gly Leu His Ile
                660                 665                 670

Ala Ile Leu Pro Ile Leu Thr Leu Asp Val Pro Leu Pro Asp Gln Leu
                675                 680                 685

Pro Leu Gln Glu Ile Asp Thr Leu Ser Arg Phe His His Leu Ala Ser
                690                 695                 700

Thr Ile Gly Arg Leu Ser Gly Asp Met Asn Ala Tyr Lys Ile Asp Leu
705                 710                 715                 720

Ala His Gly Glu Glu Ser Ser Cys Ile Ser Cys Tyr Met Lys Asp Asn
                    725                 730                 735

Pro Gly Thr Thr Glu Gly Asp Ala His Asn Tyr Ala Asn Val Thr Ile
                740                 745                 750

Ser Tyr Leu Met Lys Glu Leu Asn Leu Glu Leu Met Gly Gln His Asn
                755                 760                 765

Arg Val Ser Phe Leu Arg Thr Ser Lys Lys Pro Ala Phe Asp Ile Tyr
                770                 775                 780

Arg Ala Ser Asn Tyr Met Tyr Lys Tyr Arg Asp Gly Tyr Thr Ile Ala
785                 790                 795                 800

Asp Lys Glu Thr Lys Asn Leu Val Met Arg Thr Leu Val Gln Ala Val
                    805                 810                 815

Ser Leu

<210> SEQ ID NO 4
<211> LENGTH: 10
<212> TYPE: PRT
<213> ORGANISM: Psuedolarix amabilis

<400> SEQUENCE: 4

Ile Asp Asp Ile Tyr Asp Thr Tyr Gly Thr
```

<210> SEQ ID NO 5
<211> LENGTH: 5
<212> TYPE: PRT
<213> ORGANISM: Psuedolarix amabilis

<400> SEQUENCE: 5

Asp Asp Ile Tyr Asp
1               5

<210> SEQ ID NO 6
<211> LENGTH: 9
<212> TYPE: PRT
<213> ORGANISM: Psuedolarix amabilis

<400> SEQUENCE: 6

Gly Asp Met Asn Ala Tyr Lys Ile Asp
1               5

<210> SEQ ID NO 7
<211> LENGTH: 25
<212> TYPE: DNA
<213> ORGANISM: Artificial Sequence
<220> FEATURE:
<223> OTHER INFORMATION: synthetic primer sequence

<400> SEQUENCE: 7
tatcatatgg ctggcgtttc tgttg                                    25

<210> SEQ ID NO 8
<211> LENGTH: 28
<212> TYPE: DNA
<213> ORGANISM: Artificial Sequence
<220> FEATURE:
<223> OTHER INFORMATION: synthetic primer sequence

<400> SEQUENCE: 8
tatgtcgact aaagtggga gcggatca                                  28

<210> SEQ ID NO 9
<211> LENGTH: 27
<212> TYPE: DNA
<213> ORGANISM: Artificial Sequence
<220> FEATURE:
<223> OTHER INFORMATION: synthetic primer sequence

<400> SEQUENCE: 9
tatcatatga tacggtcaaa tacttcg                                  27

<210> SEQ ID NO 10
<211> LENGTH: 27
<212> TYPE: DNA
<213> ORGANISM: Artificial Sequence
<220> FEATURE:
<223> OTHER INFORMATION: synthetic primer sequence

<400> SEQUENCE: 10
tgagagctct cataaagaca cagcttg                                  27

<210> SEQ ID NO 11
<211> LENGTH: 26
<212> TYPE: DNA
<213> ORGANISM: Artificial Sequence
<220> FEATURE:
<223> OTHER INFORMATION: synthetic primer sequence

<400> SEQUENCE: 11
ccacgtttct atgtgcagtg aacctc                                            26

<210> SEQ ID NO 12
<211> LENGTH: 26
<212> TYPE: DNA
<213> ORGANISM: Artificial Sequence
<220> FEATURE:
<223> OTHER INFORMATION: synthetic primer sequence

<400> SEQUENCE: 12
gaggttcact gcacatagaa acgtgg                                            26

<210> SEQ ID NO 13
<211> LENGTH: 28
<212> TYPE: DNA
<213> ORGANISM: Artificial Sequence
<220> FEATURE:
<223> OTHER INFORMATION: synthetic primer sequence

<400> SEQUENCE: 13
atgtaaacca atcgtgacct tgctgttc                                          28

<210> SEQ ID NO 14
<211> LENGTH: 28
<212> TYPE: DNA
<213> ORGANISM: Artificial Sequence
<220> FEATURE:
<223> OTHER INFORMATION: synthetic primer sequence

<400> SEQUENCE: 14
gaacagcaag gtcacgattg gtttacat                                          28

<210> SEQ ID NO 15
<211> LENGTH: 30
<212> TYPE: DNA
<213> ORGANISM: Artificial Sequence
<220> FEATURE:
<223> OTHER INFORMATION: synthetic primer sequence

<400> SEQUENCE: 15
ctatatgtaa accaaccgtg accttgctgt                                        30

<210> SEQ ID NO 16
<211> LENGTH: 30
<212> TYPE: DNA
<213> ORGANISM: Artificial Sequence
<220> FEATURE:
<223> OTHER INFORMATION: synthetic primer sequence

<400> SEQUENCE: 16
acagcaaggt cacggttggt ttacatatag                                        30

<210> SEQ ID NO 17
<211> LENGTH: 33
<212> TYPE: DNA
<213> ORGANISM: Artificial Sequence
<220> FEATURE:
<223> OTHER INFORMATION: synthetic primer sequence

<400> SEQUENCE: 17
atcgctatat gtaaactact cgtgaccttg ctg                                    33

<210> SEQ ID NO 18

```
<211> LENGTH: 33
<212> TYPE: DNA
<213> ORGANISM: Artificial Sequence
<220> FEATURE:
<223> OTHER INFORMATION: synthetic primer sequence

<400> SEQUENCE: 18
cagcaaggtc acgagtagtt tacatatagc gat                                    33

<210> SEQ ID NO 19
<211> LENGTH: 24
<212> TYPE: DNA
<213> ORGANISM: Artificial Sequence
<220> FEATURE:
<223> OTHER INFORMATION: synthetic primer sequence

<400> SEQUENCE: 19
ccatagtgta agtttccacg tttc                                              24

<210> SEQ ID NO 20
<211> LENGTH: 24
<212> TYPE: DNA
<213> ORGANISM: Artificial Sequence
<220> FEATURE:
<223> OTHER INFORMATION: synthetic primer sequence

<400> SEQUENCE: 20
gaaacgtgga aacttacact atgg                                              24

<210> SEQ ID NO 21
<211> LENGTH: 24
<212> TYPE: DNA
<213> ORGANISM: Artificial Sequence
<220> FEATURE:
<223> OTHER INFORMATION: synthetic primer sequence

<400> SEQUENCE: 21
ccatagtgta aacttccacg tttc                                              24

<210> SEQ ID NO 22
<211> LENGTH: 24
<212> TYPE: DNA
<213> ORGANISM: Artificial Sequence
<220> FEATURE:
<223> OTHER INFORMATION: synthetic primer sequence

<400> SEQUENCE: 22
gaaacgtgga agtttacact atgg                                              24

<210> SEQ ID NO 23
<211> LENGTH: 24
<212> TYPE: DNA
<213> ORGANISM: Artificial Sequence
<220> FEATURE:
<223> OTHER INFORMATION: synthetic primer sequence

<400> SEQUENCE: 23
ccatagtgta aaattccacg tttc                                              24

<210> SEQ ID NO 24
<211> LENGTH: 24
<212> TYPE: DNA
<213> ORGANISM: Artificial Sequence
<220> FEATURE:
<223> OTHER INFORMATION: synthetic primer sequence

<400> SEQUENCE: 24
```

-continued gaaacgtgga attttacact atgg					24

<210> SEQ ID NO 25
<211> LENGTH: 34
<212> TYPE: DNA
<213> ORGANISM: Artificial Sequence
<220> FEATURE:
<223> OTHER INFORMATION: synthetic primer sequence

<400> SEQUENCE: 25
gtgaggatgg gcaatataca tatatgtaaa ccac					34

<210> SEQ ID NO 26
<211> LENGTH: 34
<212> TYPE: DNA
<213> ORGANISM: Artificial Sequence
<220> FEATURE:
<223> OTHER INFORMATION: synthetic primer sequence

<400> SEQUENCE: 26
gtggtttaca tatatgtata ttgcccatcc tcac					34

<210> SEQ ID NO 27
<211> LENGTH: 32
<212> TYPE: DNA
<213> ORGANISM: Artificial Sequence
<220> FEATURE:
<223> OTHER INFORMATION: synthetic primer sequence

<400> SEQUENCE: 27
gatgggcaat atcagtatat gtaaaccact cg					32

<210> SEQ ID NO 28
<211> LENGTH: 32
<212> TYPE: DNA
<213> ORGANISM: Artificial Sequence
<220> FEATURE:
<223> OTHER INFORMATION: synthetic primer sequence

<400> SEQUENCE: 28
cgagtggttt acatatactg atattgccca tc					32

<210> SEQ ID NO 29
<211> LENGTH: 18
<212> TYPE: DNA
<213> ORGANISM: Artificial Sequence
<220> FEATURE:
<223> OTHER INFORMATION: synthetic primer sequence

<400> SEQUENCE: 29
ggcaauaagg cggcgcgg					18

<210> SEQ ID NO 30
<211> LENGTH: 25
<212> TYPE: DNA
<213> ORGANISM: Artificial Sequence
<220> FEATURE:
<223> OTHER INFORMATION: synthetic primer sequence

<400> SEQUENCE: 30
ggaauaaagg ggagcggaca aagac					25

<210> SEQ ID NO 31
<211> LENGTH: 22
<212> TYPE: DNA

```
<213> ORGANISM: Artificial Sequence
<220> FEATURE:
<223> OTHER INFORMATION: synthetic primer sequence

<400> SEQUENCE: 31
ggcauuaagc aagaacacgc gc                                           22

<210> SEQ ID NO 32
<211> LENGTH: 24
<212> TYPE: DNA
<213> ORGANISM: Artificial Sequence
<220> FEATURE:
<223> OTHER INFORMATION: synthetic primer sequence

<400> SEQUENCE: 32
ggaauaaaag acacagcgaa cgag                                         24

<210> SEQ ID NO 33
<211> LENGTH: 54
<212> TYPE: DNA
<213> ORGANISM: Artificial Sequence
<220> FEATURE:
<223> OTHER INFORMATION: synthetic primer sequence

<400> SEQUENCE: 33
gaattcaacc ctcactaaag ggcggccgca tgacgaaaag gagtgaagca gatg        54

<210> SEQ ID NO 34
<211> LENGTH: 59
<212> TYPE: DNA
<213> ORGANISM: Artificial Sequence
<220> FEATURE:
<223> OTHER INFORMATION: synthetic primer sequence

<400> SEQUENCE: 34
cttgtaatcc atcgatacta gtgcggccgc ttataaagac acagcttgaa cgagagttc   59

<210> SEQ ID NO 35
<211> LENGTH: 40
<212> TYPE: PRT
<213> ORGANISM: Artificial Sequence
<220> FEATURE:
<223> OTHER INFORMATION: synthetic alignment sequence

<400> SEQUENCE: 35

Met Arg Phe Arg His Arg Asn Val Glu Tyr Tyr Thr Met Ala Ser Cys
1               5                   10                  15

Ile Ala Met Ile Asp Asp Ile Tyr Asp Thr Tyr Gly Thr Ser Lys Val
            20                  25                  30

Thr Ser Gly Leu His Ile Ala Arg
        35                  40

<210> SEQ ID NO 36
<211> LENGTH: 41
<212> TYPE: PRT
<213> ORGANISM: Artificial Sequence
<220> FEATURE:
<223> OTHER INFORMATION: synthetic alignment sequence

<400> SEQUENCE: 36

Phe Thr Phe Ala Arg Glu Arg Pro Leu Glu Phe Tyr Phe Leu Val Ala
1               5                   10                  15

Thr Gly Thr Tyr Leu Asp Asp Met Tyr Asp Thr Tyr Gly Thr Gly Ile
            20                  25                  30
```

Thr Ser Ile Gly Gln Arg Ile Leu Arg
        35                  40

<210> SEQ ID NO 37
<211> LENGTH: 41
<212> TYPE: PRT
<213> ORGANISM: Artificial Sequence
<220> FEATURE:
<223> OTHER INFORMATION: synthetic alignment sequence

<400> SEQUENCE: 37

Phe Thr Phe Ala Arg Glu Arg Pro Leu Glu Phe Tyr Phe Leu Val Ala
1               5                   10                  15

Ala Gly Thr Tyr Leu Asp Asp Met Tyr Asp Thr Tyr Gly Thr Gly Ile
            20                  25                  30

Thr Ser Ile Gly Gln Arg Ile Leu Arg
        35                  40

<210> SEQ ID NO 38
<211> LENGTH: 41
<212> TYPE: PRT
<213> ORGANISM: Artificial Sequence
<220> FEATURE:
<223> OTHER INFORMATION: synthetic alignment sequence

<400> SEQUENCE: 38

Leu Asn Phe Thr Arg Glu Arg Val Thr Glu Ile Tyr Phe Ser Pro Ala
1               5                   10                  15

Ser Phe Ile Phe Leu Asp Asp Leu Tyr Asp Ala His Gly Ser Ala Ser
            20                  25                  30

Val Ser Ile Ala Leu Gly Thr Val Arg
        35                  40

<210> SEQ ID NO 39
<211> LENGTH: 41
<212> TYPE: PRT
<213> ORGANISM: Artificial Sequence
<220> FEATURE:
<223> OTHER INFORMATION: synthetic alignment sequence

<400> SEQUENCE: 39

Leu Lys Phe Thr Arg Glu Arg Val Thr Glu Ile Tyr Phe Ser Pro Ala
1               5                   10                  15

Ser Phe Met Phe Leu Asp Asp Leu Tyr Asp Ala His Gly Ser Ala Ser
            20                  25                  30

Val Ser Ile Ala Leu Gly Thr Val Arg
        35                  40

<210> SEQ ID NO 40
<211> LENGTH: 41
<212> TYPE: PRT
<213> ORGANISM: Artificial Sequence
<220> FEATURE:
<223> OTHER INFORMATION: synthetic alignment sequence

<400> SEQUENCE: 40

Leu Lys Phe Thr Arg Glu Arg Val Thr Glu Ile Tyr Phe Ser Ala Ala
1               5                   10                  15

Ser Phe Ile Phe Leu Asp Asp Leu Tyr Asp Ala His Gly Ser Ala Ser
            20                  25                  30

Val Ser Ile Ser Leu Gly Thr Leu Arg
        35                  40

```
<210> SEQ ID NO 41
<211> LENGTH: 41
<212> TYPE: PRT
<213> ORGANISM: Artificial Sequence
<220> FEATURE:
<223> OTHER INFORMATION: synthetic alignment sequence

<400> SEQUENCE: 41

Leu Asn Phe Thr Arg Asp Arg Val Ala Glu Ile Phe Phe Ser Ile Ala
1               5                   10                  15

Ser Ser Met Phe Leu Asp Asp Leu Tyr Asp Ala His Gly Ser Ala Ser
            20                  25                  30

Val Ser Ile Ala Gly Ala Thr Leu Arg
        35                  40

<210> SEQ ID NO 42
<211> LENGTH: 41
<212> TYPE: PRT
<213> ORGANISM: Artificial Sequence
<220> FEATURE:
<223> OTHER INFORMATION: synthetic alignment sequence

<400> SEQUENCE: 42

Leu Lys Phe Thr Arg Asp Arg Val Val Glu Thr Tyr Phe Ala Val Ala
1               5                   10                  15

Ser Ser Met Phe Leu Asp Asp Leu Tyr Asp Gly Tyr Gly Ser Ala Gln
            20                  25                  30

Val Ser Ile Gly Val Ala Thr Ile Arg
        35                  40

<210> SEQ ID NO 43
<211> LENGTH: 39
<212> TYPE: PRT
<213> ORGANISM: Artificial Sequence
<220> FEATURE:
<223> OTHER INFORMATION: synthetic alignment sequence

<400> SEQUENCE: 43

Ile Asn Phe Thr Arg His Arg Val Ala Glu Val Tyr Phe Ser Ser Ala
1               5                   10                  15

Thr Phe Phe Asp Asp Met Ala Asp Ile Phe Ala Thr Tyr Ala Ile Ser
            20                  25                  30

Val Gly Leu Gly Pro Cys Arg
        35
```

DITERPENE SYNTHASES AND THEIR USE FOR PRODUCTION OF DITERPENES

CROSS-REFERENCES TO RELATED APPLICATIONS

The present invention is a U.S. National Phase Application of PCT/US2017/043786, International Filing Date Jul. 25, 2017, which claims benefit of priority to U.S. Provisional Application No. 62/367,264, filed Jul. 27, 2016, which are incorporated by reference for all purposes.

REFERENCE TO SUBMISSION OF A SEQUENCE LISTING AS A TEXT FILE

The sequence listing written in file Seq_Listing_081906-1123423.txt created on Jan. 18, 2019, 28,672 bytes, machine format IBM-PC, MS-Windows operating system, is hereby incorporated by reference in its entirety for all purposes.

BRIEF SUMMARY OF INVENTION

The diversity of small molecules produced via plant diterpene metabolism offers a plethora of known and potentially novel therapeutics. Among these, the microtubule-destabilizing activity of pseudolaric acid B (PAB) holds promise for new anticancer agents. PAB is found, perhaps uniquely, in the roots of the coniferous tree golden larch (*Pseudolarix amabilis*, Pxa).

In one aspect, the present invention provides an isolated nucleic acid molecule, comprising a sequence of nucleotides encoding a diterpene synthase polypeptide selected from among: a) a polypeptide whose sequence is set forth in SEQ ID NO:1 or is at least 85%, 90%, 95%, or 99% identical to the sequence set forth in SEQ ID NO:1; b) a polypeptide encoded by a nucleotide sequence forth in GenBank accession number KU685114, or at least 85%, 90%, 95%, or 99% identical to the sequence set forth in GenBank accession number KU685114; c) an active fragment of the polypeptide of a) or b); and c) a polypeptide having a sequence of amino acids that has at least 95% sequence identity with a polypeptide of a), b), or c), wherein: the encoded polypeptide or active fragment catalyzes the formation of sibongilene from geranylgeranyl diphosphate (GGPP).

In some embodiments, the isolated nucleic acid is cDNA. In some embodiments, the the isolated nucleic acid encodes the diterpene synthase polypeptide whose sequence is set forth in SEQ ID NO:1. In some embodiments, the isolated nucleic acid encodes the diterpene synthase polypeptide encoded by a nucleotide sequence forth in GenBank accession number KU685114.

In another aspect, the present invention provides a vector or a host cell, or a host cell lysate, comprising one of the foregoing isolated nucleic acids. In another aspect, the present invention provides a host cell comprising an isolated nucleic acid molecule, comprising a sequence of nucleotides encoding a diterpene synthase polypeptide selected from among: a) a polypeptide whose sequence is set forth in one of SEQ ID NO:1; b) a polypeptide encoded by a nucleotide sequence forth in GenBank accession number KU685114; c) an active fragment of the polypeptide of a) or b); and c) a polypeptide having a sequence of amino acids that has at least 95% sequence identity with a polypeptide of a), b), or c), wherein: the encoded polypeptide or active fragment catalyzes the formation of sibongilene from geranylgeranyl diphosphate (GGPP), wherein the encoded diterpene synthase polypeptide is heterologous to the host cell. In some embodiments, the host cell is a prokaryotic host cell. In some embodiments, the host cell is a eukaryotic host cell. In some embodiments, the host cell is an *E. coli* cell. In some embodiments, the host cell is selected from the group consisting of a fungal, plant, insect, or amphibian host cell. In some embodiments, the host cell is an animal cell. In some embodiments, the host cell is a yeast cell. In some embodiments, the host cell produces a 7,5-fused bicyclic diterpene (e.g., a heterologous 7,5-fused bicyclic diterpene). In some embodiments, the host cell produces sibongilene.

In another aspect, the present invention provides a method of producing a 7,5-fused bicyclic diterpene, comprising: i) contacting (E,E,E)-geranylgeranyl diphosphate (GGPP) with a diterpene synthase polypeptide encoded by the nucleic acid molecule of claim 1 under conditions effective to produce the cis-7,5-fused bicyclic diterpene, wherein: contacting is effected with an isolated diterpene synthase polypeptide, or contacting is effected in a host cell comprising the nucleic acid molecule, and the nucleic acid molecule is heterologous to the host cell; and ii) optionally, isolating the 7,5-fused bicyclic diterpene produced in step i). In some embodiments the 7,5-fused bicyclic diterpene is sibongilene. In some embodiments, the method further comprises isolating the 7,5-fused bicyclic diterpene. In some embodiments, the method further comprises converting the 7,5-fused bicyclic diterpene to a pseudolaric acid. In some embodiments, the method further comprises converting the 7,5-fused bicyclic diterpene to pseudolaric acid B. In some embodiments, the method further comprises isolating the pseudolaric acid B.

In another aspect, the present invention provides a pharmaceutical composition comprising sibongilene and a pharmaceutical excipient. In another aspect, the present invention provides isolated sibongilene or a composition comprising isolated sibongilene. In another aspect, the present invention provides a host cell, host cell lysate, or host cell conditioned medium comprising sibongilene, wherein the sibongilene is heterologous to the host cell.

BRIEF DESCRIPTION OF THE DRAWINGS

[FIG. 3C] Predicted structure and stereochemistry of sibongilene.

[FIG. 4B] Protein alignment of select PxaTPS8 residues with known gymnosperm TPSs (PxaTBS8—SEQ ID NO:35, PxaTBS5—SEQ ID NO:36, AgBIS—SEQ ID NO:37, AgAS—SEQ ID NO:38, PaLAS—SEQ ID NO:39, PaISO—SEQ ID NO:40, PcPIM—SEQ ID NO:41, AbCAS—SEQ ID NO:42, and TbrTXS—SEQ ID NO:43). [FIG. 4C] Scaled extracted ion chromatograms (EIC; m/z 216) comparing sibongilene formation of PxaTPS8 variants to the wild-type (WT).

[FIG. 7C] Activity assays of PxaTPS8 with geranyl diphosphate (GPP) or farnesyl diphosphate (FPP) as substrate resulted exclusively in the corresponding dephosphorylated substrates demonstrating no conversion by PxaTPS8. GC/MS traces are illustrated as total ion chromatograms (TIC).

DEFINITIONS

Figure 1:
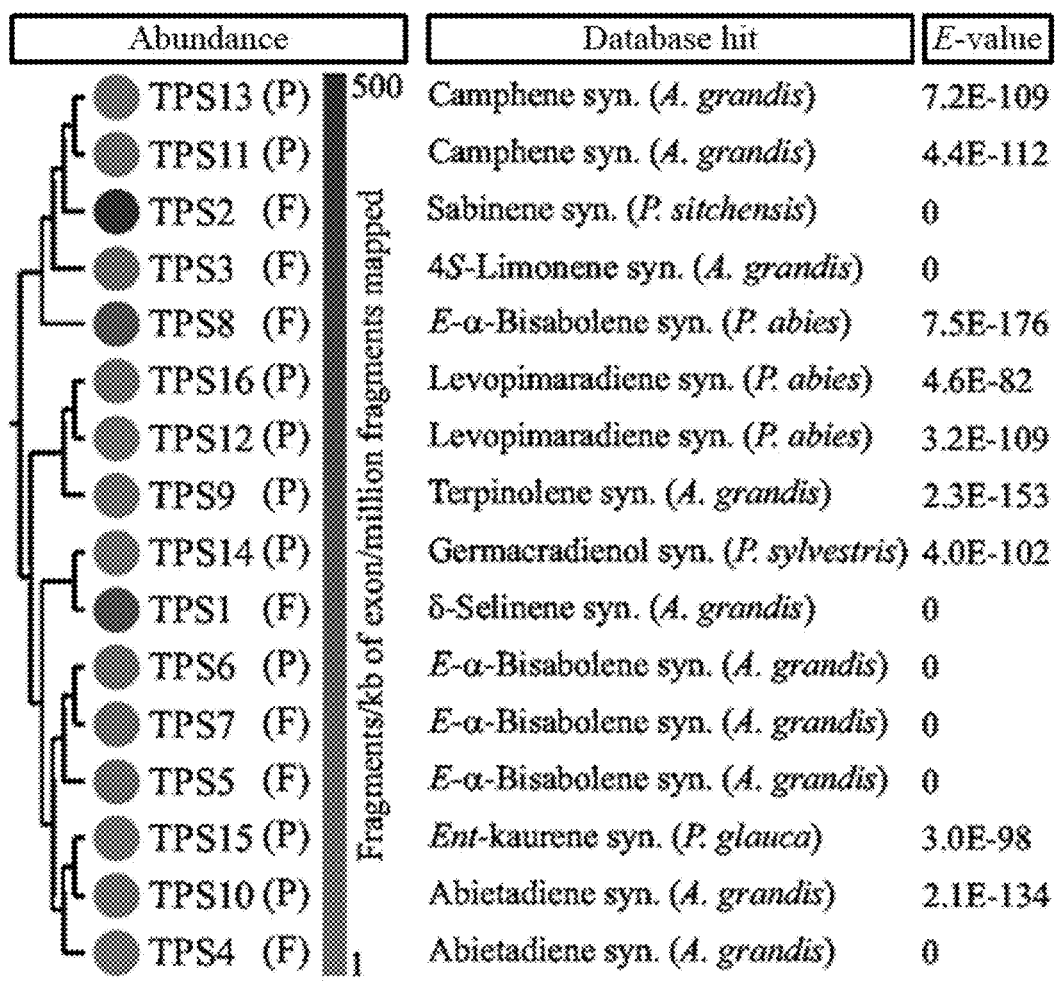
FIG. 1. Annotation of TPS genes in the root-specific transcriptome of *P. amabilis* (E-value threshold 1E-50). Relative transcript abundance is based on FPKM values obtained via mapping of Illumina reads against assembled TPS reads. P, partial transcript; F, full length transcript.

Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet may not be permanent, but equivalent information can be found by searching the internet. Reference thereto evidences the availability and public dissemination of such information.

As used herein, a diterpenoid is an unsaturated hydrocarbon based on the isoprene unit ($C_5F_{18}$), and having a core structure of the general formula $C_{5x}H_{8x}$. A diterpene contains a 20 carbon atom core structure, and hence is made up of four isoprene units. A diterpenoid also is a type of diterpene. A diterpenoid can derive from geranylgeranyl pyrophosphate (GGPP). Diterpenoids include diterpene olefins (e.g., sibongilene), deiterpene acids (e.g., pseudolaric acids, such as pseudolaric acid B), and diterpene alcohols.

As used herein, "diterpene synthase" or "diTPS" as used herein, refers to a monofunctional diterpene synthase that is capable of synthesizing a diterpene olefin by sequential cycloisomerisation of the substrate (E,E,E)-geranylgeranyl diphosphate (GGPP).

As used herein, monofunctional class I diTPS refers to a monofunctional synthase that contains a class I active site that has a $Mg^{2+}$ coordinating DDxxD motif and NSE/DTE motifs.

As used herein, an active fragment of a synthase polypeptide refers to a contiguous sequence of amino acids of a synthase polypeptide that exhibits synthase activity (e.g. 5,7-fused bicyclic synthase activity such as sibongilene synthase activity), but that does not include the full-sequence of the synthase polypeptide. For purposes herein, the active fragment typically includes the class I site that has a a DDxxD motif, and more typically a DDxxD motif and NSE/DTE motifs. The active fragment generally contains at least 300, 400, 500, 600, 700, 800 or more amino acid residues.

As used herein, "sibongilene synthase activity" refers to a synthase polypeptide or an active fragment of a synthase polypeptide that catalyzes the formation of sibongilene from geranylgeranyl diphosphate (GGPP).

As used herein, a pseudomature polypeptide with reference to a synthase refers to a polypeptide that lacks one or more amino acid residues from the N-terminus of the preprotein, and typically, or typically at least 10, 20, 26, 30, 40, 50, 60, 70, 80, 90 or more N-terminal amino acid residues. Typically, a pseudomature polypeptide lacks the plastidial transit peptide. For example, with reference to PxaTPS8, the plastidial transit polypeptide corresponds to amino acid residues 1-28 of SEQ ID NO:1. Hence, a pseudomature PxaTPS8 polypeptide lacks at least 28, 30, 40, 50, 55, 60, 65, 70, 75, 80, 90 or more N-terminal amino acid residues of the preprotein set forth in SEQ ID NO:1. In some embodiments, the pseudomature PxaTPS8 polypeptide has the sequence set forth in SEQ ID NO:3.

As used herein, sibongilene is the compound having the following structure or a mixture of isomers thereof:

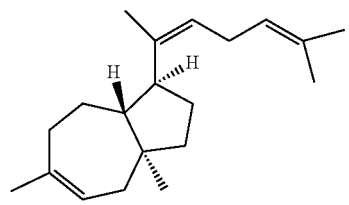 [SMILES: CC(C)=CC/C=C(/C)[C@H]1CC[C@@]2(C)CC=C(C)CC[C@H]12]

As used herein, corresponding residues refers to residues that occur at aligned loci. Related or variant polypeptides are aligned by any method known to those of skill in the art. Such methods typically maximize matches, and include methods such as manual alignments and those produced by the numerous alignment programs available (for example, BLASTP) and others known to those of skill in the art. By aligning the sequences of polypeptides, one skilled in the art can identify corresponding residues, using conserved and identical amino acid residues as guides. Corresponding positions also can be based on structural alignments, for example by using computer simulated alignments of protein structure.

As used herein, nucleic acids or nucleic acid molecules include DNA, RNA and analogs thereof, including peptide nucleic acids (PNA) and mixtures thereof. Nucleic acids can be single or double-stranded.

As used herein, the term polynucleotide means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term nucleotides is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule cannot be paired. Such unpaired ends will, in general, not exceed 20 nucleotides in length.

As used herein, a peptide refers to a polypeptide that is greater than or equal to 2 amino acids in length, and less than or equal to 40 amino acids in length.

As used herein, the amino acids which occur in the various sequences of amino acids provided herein are identified according to their known, three-letter or one-letter abbreviations. The nucleotides which occur in the various nucleic acid fragments are designated with the standard single-letter designations used routinely in the art.

As used herein, an "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

As used herein, "amino acid residue" refers to an amino acid formed upon chemical digestion (hydrolysis) of a polypeptide at its peptide linkages. The amino acid residues described herein are presumed to be in the "L" isomeric form. Residues in the "D" isomeric form, which are so designated, can be substituted for any L-amino acid residue as long as the desired functional property is retained by the polypeptide. $NH_2$ refers to the free amino group present at the amino terminus of a polypeptide. COOH refers to the free carboxy group present at the carboxyl terminus of a polypeptide.

All amino acid residue sequences represented herein by formulae have a left to right orientation in the conventional direction of amino-terminus to carboxyl-terminus. In addition, the phrase "amino acid residue" is defined to include the twenty naturally occurring and proteinogenic amino acids and modified and unusual amino acids, such as those referred to in 37 C.F.R. §§ 1.821-1.822, and incorporated herein by reference. Furthermore, it should be noted that a dash at the beginning or end of an amino acid residue sequence indicates a peptide bond to a further sequence of one or more amino acid residues, to an amino-terminal group such as $NH_2$ or to a carboxyl-terminal group such as COOH.

As used herein, "naturally occurring amino acids" refer to the 20 L-amino acids that occur in polypeptides.

As used herein, "non-natural amino acid" refers to an organic compound containing an amino group and a carboxylic acid group that is not one of the naturally-occurring amino acids. Non-naturally occurring amino acids thus include, for example, amino acids or analogs of amino acids other than the 20 naturally-occurring amino acids and include, but are not limited to, the D-isostereomers of amino acids. Exemplary non-natural amino acids are known to those of skill in the art.

As used herein, modification is in reference to modification of the primary sequence of amino acids of a polypeptide or a sequence of nucleotides in a nucleic acid molecule and includes deletions, insertions, and replacements and rearrangements of amino acids and nucleotides. Modifications can be made by making conservative amino acid replacements and also non-conservative amino acid substitutions as well as by insertions and other such changes in primary sequence. Modifications also can include post-translational modifications or other changes to the molecule that can occur due to conjugation or linkage, directly or indirectly, to another moiety, but when such modifications are contemplated they are referred to as post-translational modifications or conjugates or other such term as appropriate. Methods of modifying a polypeptide are routine to those of skill in the art, and can be performed by standard methods, such as site directed mutations, amplification methods, and gene shuffling methods.

As used herein, amino acid replacements or substitutions contemplated include, but are not limited to, conservative substitutions, including, but not limited to, those set forth in Table 1. Suitable conservative substitutions of amino acids are known to those of skill in the art and can be made generally without altering the conformation or activity of the polypeptide. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. co., p. 224). Conservative amino acid substitutions are made, for example, in accordance with those set forth in Table 1 as follows:

TABLE 1

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |

TABLE 1-continued

| Original residue | Conservative substitution |
| --- | --- |
| Trp (W) | Tyr |
| Tyr (Y) | Trp; Phe |
| Val (V) | Ile; Leu; Met |

Other conservative substitutions also are permissible and can be determined empirically or in accord with known conservative substitutions.

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, a DNA segment is a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, "primary sequence" refers to the sequence of amino acid residues in a polypeptide.

As used herein, "similarity" between two proteins or nucleic acids refers to the relatedness between the sequence of amino acids of the proteins or the nucleotide sequences of the nucleic acids. Similarity can be based on the degree of identity and/or homology of sequences of residues and the residues contained therein. Methods for assessing the degree of similarity between proteins or nucleic acids are known to those of skill in the art. For example, in one method of assessing sequence similarity, two amino acid or nucleotide sequences are aligned in a manner that yields a maximal level of identity between the sequences. "Identity" refers to the extent to which the amino acid or nucleotide sequences are invariant. Alignment of amino acid sequences, and to some extent nucleotide sequences, also can take into account conservative differences and/or frequent substitutions in amino acids (or nucleotides). Conservative differences are those that preserve the physico-chemical properties of the residues involved. Alignments can be global (alignment of the compared sequences over the entire length of the sequences and including all residues) or local (the alignment of a portion of the sequences that includes only the most similar region or regions).

As used herein, "sequence identity" refers to the number of identical or similar amino acids or nucleotide bases in a comparison between a test and a reference polypeptide or polynucleotide. Sequence identity can be determined by sequence alignment of nucleic acid or protein sequences to identify regions of similarity or identity. For purposes herein, sequence identity is generally determined by alignment to identify identical residues. The alignment can be local or global. Matches, mismatches and gaps can be identified between compared sequences. Gaps are null amino acids or nucleotides inserted between the residues of aligned sequences so that identical or similar characters are aligned. Generally, there can be internal and terminal gaps. Sequence identity can be determined by taking into account gaps as the number of identical residues/length of the shortest sequence×100. When using gap penalties, sequence identity can be determined with no penalty for end gaps (e.g. terminal gaps are not penalized). Alternatively, sequence identity can be determined without taking into account gaps as the number of identical positions/length of the total aligned sequence×100.

Amino acid sequence similarity or identity can be computed by using the BLASTP and TBLASTN programs which employ the BLAST (basic local alignment search tool) 2.0 algorithm. Techniques for computing amino acid sequence similarity or identity are well known to those skilled in the art, and the use of the BLAST algorithm is described in ALTSCHUL et al. 1990, *J Mol. Biol.* 215: 403-410 and ALTSCHUL et al. (1997), *Nucleic Acids Res.* 25: 3389-3402.

As used herein, the term "identity" represents a comparison between a test and a reference polypeptide or polynucleotide. In one non-limiting example, "at least 90% identical to" refers to percent identities from 90 to 100% relative to the reference polypeptides. Identity at a level of 90% or more is indicative of the fact that, assuming for exemplification purposes a test and reference polypeptide length of 100 amino acids are compared, no more than 10% (i.e., 10 out of 100) of amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences also can be due to deletions or truncations of amino acid or nucleotide residues. Differences are defined as nucleic acid or amino acid substitutions, insertions or deletions. Depending on the length of the compared sequences, at the level of homologies or identities above about 85-90%, the result reasonably independent of the program and gap parameters set; such high levels of identity can be assessed readily, often without relying on software.

As used herein, a substantially similar sequence is an amino acid sequence that differs from a reference sequence only by one or more conservative substitutions. Such a sequence can, for example, be functionally homologous to another substantially similar sequence. It will be appreciated by a person of skill in the art the aspects of the individual amino acids in a peptide provided herein that can be substituted.

As used herein, an aligned sequence refers to the use of homology (similarity and/or identity) to align corresponding positions in a sequence of nucleotides or amino acids. Typically, two or more sequences that are related by about or 50% or more identity are aligned. An aligned set of sequences refers to 2 or more sequences that are aligned at corresponding positions and can include aligning sequences derived from RNAs, such as ESTs and other cDNAs, aligned with genomic DNA sequence.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound can, however, be a mixture of stereoisomers or isomers. In such instances, further purification might increase the specific activity of the compound.

As used herein, isolated or purified polypeptide or protein or biologically-active portion thereof is substantially free of cellular material or other contaminating proteins from the cell of tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as proteolytic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound.

As used herein, substantially free of cellular material includes preparations of diTPSs or diterpene products in which the synthase or product is separated from cellular components of the cells from which it is isolated or produced. In one embodiment, the term substantially free of cellular material includes preparations of having less that about or less than 30%, 20%, 10%, 5% or less (by dry weight) of non-diTPS or diterpene product, including cell culture medium. When the synthase is recombinantly produced, it also is substantially free of culture medium, i.e., culture medium represents less than about or at 20%, 10% or 5% of the volume of the synthase protein preparation.

As used herein, the term substantially free of chemical precursors or other chemicals includes preparations of synthase proteins or diterpene products that is separated from chemical precursors or other chemicals that are involved in the synthesis thereof. The term includes preparations of synthase proteins or diterpene products having less than about or less than 30% (by dry weight), 20%, 10%, 5% or less of chemical precursors or non-synthase chemicals or components. As described herein, the present invention can provide isolated sibongilene, or a composition containing isolated sibongilene, wherein, e.g., the isolated sibongilene is substantially free of chemical precursors or other chemicals. Similarly, the present invention can provide isolated PxaTPS8 polypeptide, or an active fragment thereof, wherein, e.g., the isolated PxaTPS8 polypeptide, or active fragment thereof, is substantially free of chemical precursors or other chemicals.

As used herein, synthetic, with reference to, for example, a synthetic nucleic acid molecule or a synthetic gene or a synthetic peptide refers to a nucleic acid molecule or polypeptide molecule that is produced by recombinant methods and/or by chemical synthesis methods.

As used herein, production by recombinant methods by using recombinant DNA methods refers to the use of the well-known methods of molecular biology for expressing proteins encoded by cloned DNA.

As used herein, vector (or plasmid) refers to discrete DNA elements that are used to introduce heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as bacterial artificial chromosomes, yeast artificial chromosomes and mammalian artificial chromosomes. Selection and use of such vehicles are well known to those of skill in the art.

As used herein, expression refers to the process by which nucleic acid is transcribed into mRNA and translated into peptides, polypeptides, or proteins. If the nucleic acid is derived from genomic DNA, expression can, if an appropriate eukaryotic host cell or organism is selected, include processing, such as splicing of the mRNA.

As used herein, an expression vector includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, vector also includes "virus vectors" or "viral vectors." Viral vectors are engineered viruses that are operatively linked to exogenous genes to transfer (as vehicles or shuttles) the exogenous genes into cells. Viral vectors include, but are not limited to, adenoviral vectors, retroviral vectors and vaccinia virus vectors.

As used herein, operably or operatively linked when referring to DNA segments means that the segments are arranged so that they function in concert for their intended purposes, e.g., transcription initiates downstream of the promoter and upstream of any transcribed sequences. The promoter is usually the domain to which the transcriptional machinery binds to initiate transcription and proceeds through the coding segment to the terminator.

As used herein, the term assessing or determining includes quantitative and qualitative determination in the sense of obtaining an absolute value for the activity of a product, and also of obtaining an index, ratio, percentage, visual or other value indicative of the level of the activity. Assessment can be direct or indirect.

As used herein, recitation that a polypeptide "consists essentially" of a recited sequence of amino acids means that only the recited portion, or a fragment thereof, of the full-length polypeptide is present. The polypeptide can optionally, and generally will, include additional amino acids from another source or can be inserted into another polypeptide.

As used herein, the term "heterologous" in reference to two different components refers to the two different components that are not found together in nature. For example, a diterpenoid such as sibongilene that is heterologous to a host cell, or lysate or conditioned medium thereof, in which it is found refers to a host cell, or lysate or conditioned medium thereof, that does not naturally produce or contain sibongilene. Similarly, a nucleic acid that is heterologous to a promoter to which it is operably linked is not found in nature to be operably linked to such promoter.

Pharmaceutically acceptable excipient" refers to a substance that aids the administration of an active agent to and absorption by a subject. Pharmaceutical excipients useful in the present invention include, but are not limited to, carriers, binders, fillers, disintegrants, lubricants, coatings, sweeteners, flavors and colors. One of skill in the art will recognize that other pharmaceutical excipients are useful in the present invention.

As used herein, the singular forms "a", "an" and "the" include plural referents unless the context clearly dictates otherwise. Thus, for example, reference to polypeptide, comprising "an amino acid replacement" includes polypeptides with one or a plurality of amino acid replacements.

As used herein, ranges and amounts can be expressed as "about" a particular value or range. About also includes the exact amount. Hence "about 5%" means "about 5%" and also "5%."

As used herein, "optional" or "optionally" means that the subsequently described event or circumstance does or does not occur, and that the description includes instances where said event or circumstance occurs and instances where it does not. For example, an optional step of isolating a diterpenoid (e.g. pseudolaric acid B) means that the diterpenoid (e.g. pseudolaric acid B) is isolated or is not isolated.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

For clarity of disclosure, and not by way of limitation, the detailed description is divided into the subsections that follow.

DETAILED DESCRIPTION OF THE INVENTION

I. Introduction

Diterpenes play essential roles in plant biology and serve as important bioproducts and therapeutics, including the anticancer drug Taxol®. Enzymes of the diterpene synthase family produce the many core structural scaffolds that form the foundation of the large diversity of biologically active diterpenes. This paper describes the discovery and mechanism of a novel diterpene synthase, sibongilene synthase, from the golden larch tree, *Pseudolarix amabilis*. The enzyme catalyzes the first committed reaction in the biosynthesis of pseudolaric acid B, a complex diterpene with potential anticancer activity.

Drawing on centuries of knowledge of ethnomedicinal plants from around the world, plant natural products, also known as secondary or specialized metabolites, remain a major yet largely untapped source for drug discovery (1). The diterpenes are one of the most diverse classes of plant secondary metabolites, including some with known functions critical to plant fitness and survival (2). These various biological activities of diterpenes also form the basis of their use as modern therapeutics, such as the anticancer drug taxol (paclitaxel) and the cAMP-activating compound forskolin (3,4).

Figure 6:
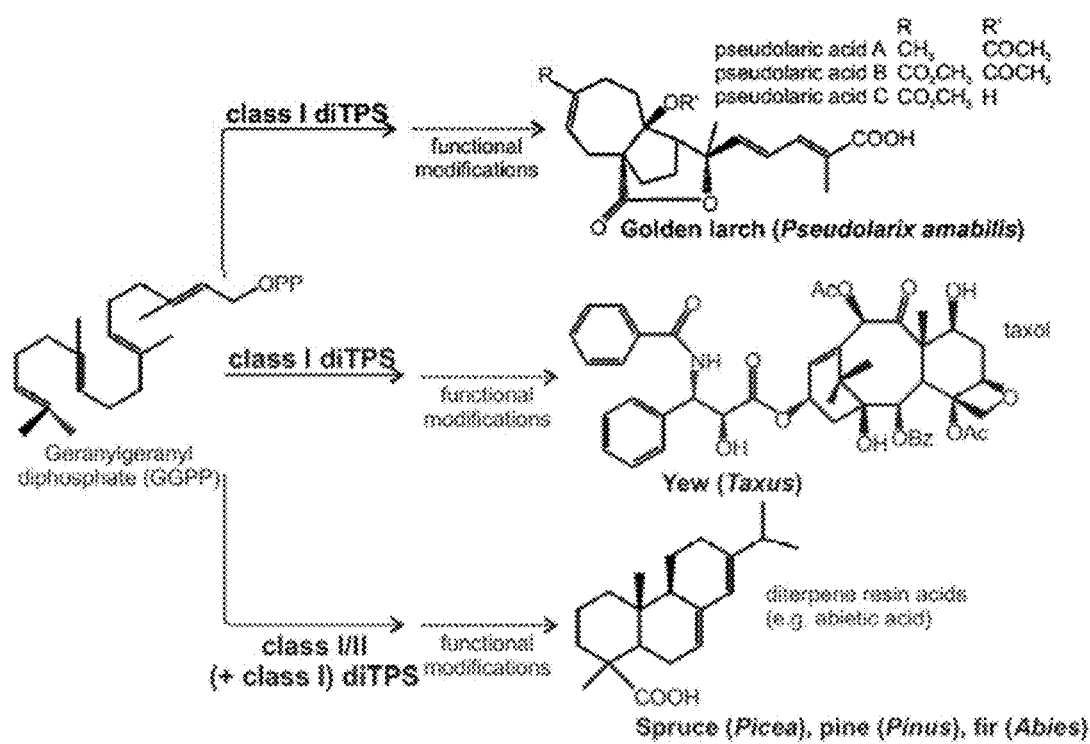
FIG. 6. Biosynthesis of specialized diterpenes in gymnosperms. Products of geranylgeranyl diphosphate (GGPP) produced by the indicated diTPS enzymes and further functional modifications are illustrated.

Golden larch (*Pseudolarix amabilis*, Pinaceae) is a deciduous gymnosperm tree renowned as one of the 50 fundamental herbs in traditional Chinese medicine. Golden larch produces a set of diterpenes with unique chemical structures among the metabolite class, the pseudolaric acids (5) (FIG. 6). The major bioactive ingredient, pseudolaric acid B (PAB), has demonstrated antitumor properties against a broad range of cancer types (6-9). Similar to the widely-used chemotherapeutics taxol and vinblastine, PAB binds to microtubules and has anti-proliferative activity (9). Specifically, PAB inhibits microtubule polymerization (9), and its activity has been shown to circumvent multidrug resistance (6,8).

Development of PAB as an anticancer drug is limited by supply, which depends on isolation from golden larch roots or may be achieved through multistep chemical synthesis (5,10). Knowledge of the genes and enzymes of PAB biosynthesis in golden larch would provide the resources needed to enable enzymatic biomanufacture. On this premise, we recently established a gene discovery strategy for diterpene metabolism in non-model plants, which is informed by metabolite and transcriptome profiling (11). Target genes include the family of diterpene synthases (diTPSs), which catalyze the carbocation-driven cyclization and rearrangement of the central precursor geranylgeranyl diphosphate (GGPP) into various diterpene scaffolds as the bedrock for diterpene structural diversity (2,12). The large number of diTPSs and their many different specific functions are the product of evolutionary diversification that involved repeated events of gene duplication and neo-functionalization (2,13). Given their shared ancestry, known plant diTPSs of different species and functions are structurally conserved with variations of three α-helical domains and two distinct active sites (N-terminal class II and C-terminal class I). Domain architecture, as well as the presence and contour of these active sites define the catalytic specificity of a given diTPS (14-16). In gymnosperms, most diTPSs of secondary metabolism are bifunctional class I/II enzymes, which contain both functional active sites and form a variety of labdane-type diterpenes (17-22) (FIG. 6). Gymnosperms also evolved monofunctional class I diTPSs with roles in secondary metabolism, including enzymes of labdane biosynthesis in pines (*Pinus*) (22) and taxadiene synthases that form the precursor for taxol and other taxoids in yew (*Taxus*) (16,23). Based on the structure of pseudolaric acids (FIG. 6), we hypothesized that a monofunctional class I diTPS may catalyze the first committed step in the biosynthesis of PAB.

Describe herein is the discovery of the first committed step in PAB biosynthesis and the underlying reaction mechanism of a novel diterpene synthase (diTPS). Analysis of the golden larch root transcriptome revealed a large TPS family, including the unusual monofunctional class I diTPS PxaTPS8, which converts geranylgeranyl diphosphate into a previously unknown 7,5-fused bicyclic diterpene, coined here sibongilene. The structure of sibongilene was elucidated by NMR combined with quantum chemical validation. Although PxaTPS8 adopts the typical 3-domain structure of diTPSs, sequence phylogeny places the enzyme with 2-domain TPSs of mono- and sesqui-terpene biosynthesis, inferring an expansive evolutionary divergence. Site-directed mutagenesis of PxaTPS8 revealed unique catalytic residues, which together with quantum chemical calculations suggested a novel carbocation-driven reaction mechanism en route to the 5,7-trans-fused bicyclic sibongilene scaffold, expanding the known diterpene structural landscape. PxaTPS8 expression in microbial and plant hosts provided proof-of-concept systems for metabolic engineering, and production of sibongilene, pseudolaric acids, such as psueudolaric acid B, and related diterpenoids.

II. Monofunctional Class I Diterpene Polypeptides and Diterpenoid Products

The present disclosure relates to one, or more than one, diterpene synthase (diTPS) nucleic acid molecule and one, or more than one, diTPS polypeptide. The one or more than one, diTPS polypeptides can be a class I diTPS. More specifically the one or more than one diTPS polypeptides can be a monofunctional class I diTPS. The diTPS can therefore contain a class I active site that has a DDxxD motif. The present disclosure provides a nucleic acid containing a nucleotide sequence encoding diterpene synthase (diTPS), for example, PxaTPS8 diTPS (SEQ ID NO:2, encoding the polypeptide SEQ ID NO:1). The nucleotide sequence encoding diTPS can be operatively linked to a regulatory region active in a host.

Also provided herein are variants of any of the nucleic acid sequences provided herein exhibiting substantially the same properties as the sequences provided herein. By this it is meant that nucleic acid sequences need not be identical to the sequence disclosed herein. Variations can be attributable to single or multiple base substitutions, deletions, or insertions or local mutations involving one or more nucleotides not substantially detracting from the properties of the nucleic acid sequence as encoding an enzyme having the activity of the diTPS as provided herein.

One, or more than one, nucleic acid encoding a diTPS are provided. The nucleic acid encoding a diTPS, such as is used in any of the described embodiments herein, can contain a nucleotide sequence that is at least 50% identical to SEQ ID NO: 2, a portion thereof that encodes an active fragment that exhibits diTPS activity or to the complement thereof. For example, the nucleic acid contains a nucleotide sequence that is at least 55%, at least 60%, at least 65%, at least 70%, at least 75%, at least 80%, at least 85%, at least 90%, such as generally at least 95% or at least 98% identical to SEQ ID NO: 2, a portion thereof that encodes an active fragment that exhibits diTPS activity or the complement thereof. The present disclosure provides nucleic acid sequences encoding for a polypeptide having a sequence selected from SEQ ID NO: 1, an active fragment thereof or sequences substantially identical thereto. For example, the provided nucleic acid sequence can encode a pseudomature form of SEQ ID NO: 1 (e.g., SEQ ID NO:3), or an active fragment thereof. The one, or more than one, nucleic acid can contain the sequence set forth in SEQ ID NO: 2, or a portion thereof that encodes an active fragment that exhibits diTPS activity, combinations thereof, or sequences substantially similar thereto. The sequence of the nucleic acid can be changed, for example, to account for codon preference in a particular host cell. In particular examples, the nucleic acid encoding a diTPS contains a nucleotide sequence set forth in SEQ ID NO: 2, or a portion thereof that encodes an active fragment or the complement thereof. In other examples, the nucleic acid encoding a diTPS is set forth in SEQ ID NO: 2, or a portion thereof that encodes an active fragment or the complement thereof.

Also provided are one, or more than one diTPS polypeptides. The polypeptide having a diTPS activity, such as intended for use in aspects of the methods provided herein, is a polypeptide having an amino acid sequence that is at least 50% identical to any of SEQ ID NO: 1, or an active fragment thereof that exhibits a diTPS activity. Such polypeptides include pseudomature forms lacking the transit peptide. For examples, among polypeptides provided herein are any that have an amino acid sequence that is at least 55%, at least 60%, at least 65%, at least 70%, at least 75%, at least 80%, at least 85%, at least 90%, such as generally at least 95% or at least 98% identical, or identical, to SEQ ID NO: 1 or SEQ ID NO:3 or an active fragment thereof that exhibits diTPS activity. The one, or more than one diTPS polypeptides can contain the sequence set forth in SEQ ID NO: 1 or SEQ ID NO:3, or an active fragment thereof that exhibits diTPS activity, or sequences having at least about 80-100% sequence similarity thereto, including any percent similarity within these ranges, such as or at least or greater than 81, 82, 83, 84, 85, 86, 87, 88, 89, 90, 91, 92, 93, 94, 95, 96, 97, 98, 99% sequence similarity thereto. The present disclosure provides nucleic acid sequences encoding for a polypeptide having a sequence selected from SEQ ID NO: 1 or SEQ ID NO:3, an active fragment thereof that exhibits diTPS activity, or sequences substantially identical thereto. In examples herein, the polypeptide contains the sequence of amino acids set forth in SEQ ID NO: 1 or SEQ ID NO:3, or an active fragment thereof that exhibits diTPS activity. In other examples, the amino acid sequence for a polypeptide provided herein is set forth in SEQ ID NO: 1 SEQ ID NO: 1 or SEQ ID NO:3, or an active fragment thereof that exhibits diTPS activity. Also provided herein are pseudomature forms of any of SEQ ID NOS:1 lacking the transit peptide, such as the polypeptide set forth in SEQ ID NO:3.

Methods of Producing Diterpenoids diTPSs are useful enzymes for the metabolic engineering of bioproducts and biofuels in yeast and *E. coli* (Bohlmann et al. (2008) *Plant J.*, 54:656-669; Peralta-Yahya et al. (2011) *Nat. Commun.*, 2:483). US Patent Application 2011/0041218 discloses a method for the production of sclareol, a compound useful in the fields of perfumery and flavoring. US Patent Application 2008/0281135 discloses a method for producing terpenes of interest in plants having glandular trichomes. The plants contain a sequence encoding a heterologous terpene synthase under the control of a promoter permitting it to be specifically expressed in the trichomes. Moreover, the pathway for producing endogenous diterpenes is blocked in the trichomes of the plants, to increase the flow in the heterologous pathway. WO 2008/007031 discloses a protein having a syn-copalyl-8-ol diphosphate synthase activity, the nucleotide sequence encoding said protein, as well as a vector and a transgenic non-human organism containing the nucleic acid.

Provided herein are methods of producing diterpenoids, such as one or more pseudolaric acids, or their precursors (e.g., sibongilene), in vitro or in vivo using the monofunctional Class I diTPSs provided herein. Depending on the diTPS used, and the one or more functionalization methods used, the diterpenoid that can be produced by the present methods are for example sibongilene, pseudolaric acid A, pseudolaric acid B, pseudolaric acid C, or a derivative thereof. In some cases, a diterpenoid such as sibongilene is produced in vivo or in vitro using a diTPS described herein, and the diterpenoid is optionally isolated and further derivatized by means of enzymatic or synthetic organic chemical derivatization.

In one example, the method for producing diterpenoids is carried out in vitro. In this case, (E,E,E)-geranylgeranyl diphosphate (GGPP) is contacted with at least one polypeptide having a diterpene synthase (diTPS) activity under conditions effective to produce diterpenoids. In performing the methods, GGPP can be added to a suspension or solution containing a diterpene synthase polypeptide, which is then incubated at optimal temperature, for example between 15 and 40° C., such as between 25 and 35° C., or at 30° C. The produced diterpenoid can optionally be isolated by methods known in the art. For example, after incubation, the one or more than one diterpene produced can be isolated from the incubated solution by standard isolation procedures, such as solvent extraction and distillation, optionally after removal of polypeptides from the solution. For example, extraction can be effected with pentane, diethyl ether, methyl tertiary butyl ether or other organic solvent. Production and quantification of the amount of the diterpene product (e.g. any one or more of sibongilene, pseudolaric acid A, pseudolaric acid B, pseudolaric acid C, or a derivative thereof) can then be determined using any method known in the art, such as column chromatography, for example liquid chromatography (e.g. LC-MS or HPLC) or gas chromatography (e.g. GC-MS), using an internal standard. For detection of diphosphate intermediates, reaction products can be dephosphorylated prior to extraction by incubation with alkaline phosphatase.

In another example, the method for producing diterpenoids is carried out in vivo. In this case, the method involves introducing into a host capable of producing GGPP, a nucleotide sequence encoding a diterpene synthase (diTPS) operatively linked with a regulatory region active in the host, and growing that host under conditions that permit the expression of the nucleic acid, thereby producing the diterpenoids. Any host cell can be used for expressing the diTPS, such as any host cell described herein. For example, the host cell can be a eukaryotic or prokaryotic host cell that produces GGPP or is modified to produce GGPP. Exemplary of host cells are bacterial host cells (e.g. *E. coli*) or fungal host cells (e.g. yeast). In such an example, it is possible to carry out the method in vivo without previously isolating the polypeptide. The reaction occurs directly within the organism or cell transformed to express said nucleic acid. The diterpene product (e.g. any one or more of sibongilene, pseudolaric acid A, pseudolaric acid B, pseudolaric acid C, or a derivative thereof) then can be extracted from the cell culture medium with an organic solvent and subsequently isolated or purified by any known method, such as column chromatography, such as liquid chromatography (e.g. LC-MS or HPLC) or gas chromatography (e.g. GC-MS), and the amount and purity of the recovered product are assessed.

The quantity of diterpene produced, such as for example sibongilene, pseudolaric acid A, pseudolaric acid B, pseudolaric acid C, or a derivative thereof, can be determined by any known standard chromatographic technique useful for separating and analyzing organic compounds. For example, production can be assayed by any known chromatographic technique useful for the detection and quantification of hydrocarbons, including, but not limited to, gas chromatography mass spectrometry (GC-MS), gas chromatography using a flame ionization detector (GC-FID), capillary GC-MS, liquid chromatography mass spectrometry (LC-MS), high performance liquid chromatography (HPLC) and column chromatography. Typically, these techniques are carried out in the presence of known internal standards which are used to quantify the amount of the terpene produced. For example, diterpenes can be identified by comparison of retention times and mass spectra to those of authentic standards for the particular diterpene in gas chromatography with mass spectrometry detection. In other examples, quantification can be achieved by gas chromatography with flame ionization detection based upon calibration curves with known amounts of authentic standards and normalization to the peak area of an internal standard. These chromatographic techniques allow for the identification of any terpene or diterpene present in the organic layer.

Nucleic Acid and Encoded diTPS Polypeptides

Provided herein are nucleic acid molecules encoding a sibongilene synthase polypeptide or an active fragment thereof, including pseudomature forms lacking the plastidial transit peptide, and the encoded polypeptides. The polypeptide or active fragment thereof catalyzes the formation of sibongilene from geranylgeranyl diphosphate (GGPP). The polypeptide having such activity, such as intended for use in aspects of the methods provided herein, is a polypeptide having an amino acid sequence that is at least 50% identical to SEQ ID NO: 1 or an active fragment thereof.

The PxaTPS8 or active fragment thereof provided herein is a diTPS that is monofunctional and contains a class I active site that has a class I active site that has DDxxD and NSE/DTE motifs, and three conserved active site arginines R558, R560, R736. The class I active site encompasses for example residues corresponding to residues 594-603, IDDIYDTYGT (SEQ ID NO:4) as set forth in SEQ ID NO: 1. The DDxxD motif corresponds to amino acid residues DDIYD 595-599 (SEQ ID NO:5) as set forth in SEQ ID NO:1. The NSE/DTE motif corresponds to GDMNAYKID (SEQ ID NO:6) residues 740-747 of SEQ ID NO:1. In one example, a diTPS provided herein is a sibongelene synthase polypeptide or active fragment thereof that contains a Y564F, 5696I, S696V, G697S or Ala701C mutation with reference to SEQ ID NO:1.

Provided herein are nucleic acid molecules that encode for a polypeptide having a sequence that is at least 50% identical to SEQ ID NO:1 or that has a sequence set forth in SEQ ID NO: 1 or sequences substantially identical thereto, or an active fragment thereof. The nucleic acid encoding a diTPS that is a sibongilene synthase, such as is used in any of the described methods herein, can contain a nucleotide sequence that is at least 50% identical to SEQ ID NO: 2 or a portion thereof that encodes an active fragment having sibongilene synthase activity, or to the complement thereof. For example, the nucleic acid contains a nucleotide sequence that is at least 55%, at least 60%, at least 65%, at least 70%, at least 75%, at least 80%, at least 85%, at least 90%, such as generally at least 95% or at least 98% identical to SEQ ID NO: 2, or a portion thereof that encodes an active fragment having sibongilene synthase activity or the complement thereof. The sequence of the nucleic acid can be changed, for example, to account for codon preference in a particular host cell.

Figures 4A, 4B:
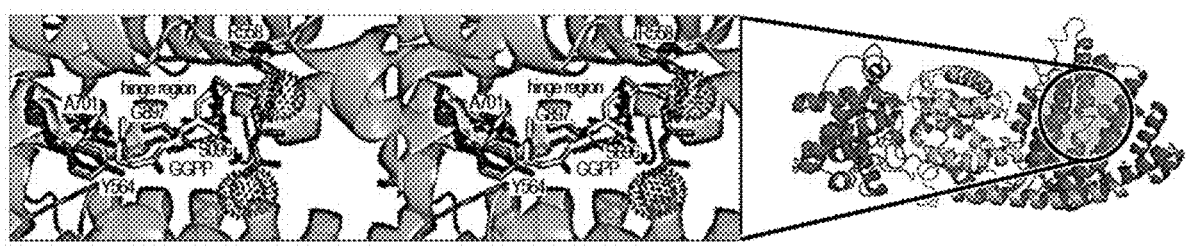
FIGS. 4A-4C [FIG. 4A] Right panel Homology model of PxaTPS8 based on the structure of *A. grandis* α-BIS (25) illustrating the typical diTPS 3-domain structure comprised of a γ- (magenta), β- (cyan) and α-domain (blue). Left panel Stereo view of the PxaTPS8 (blue) class I active site with GGPP (yellow) docked in the cavity; Mg' (cyan). Active site residues with impact on catalysis are depicted as compared to *Taxus brevifolia* TXS (orange), *A. grandis* BIS (green), *A. grandis* abietadiene synthase (purple).

Furthermore, the one or more than one diTPS polypeptides can contain modifications in active site residues as disclosed in FIG. 4B (see also Example 1). For example, the diTPS polypeptide that is a sibongilene synthase polypeptide or active fragment thereof can contain the sequence as set forth in SEQ ID NO: 1, an active fragment thereof (e.g. such as a pseudomature form as set forth in SEQ ID NO:3, or sequence substantially identical thereto, wherein the amino acid or a combination of amino acids selected from the amino acids disclosed in FIG. 4B is replaced with another amino acid. Corresponding amino acid residues in various orthologs or homologs or synthetic variants can be identified by one of skill in the art in other sequence forms of sibongilene synthase polypeptide by alignment of residues with SEQ ID NO:1.

Methods of Producing or Generating Diterpene Synthases, Vectors & Host Cells

Provided herein are polynucleotides encoding any of the diTPS provided herein or the encoded diTPSs polypeptide. As described herein, the nucleic acids and encoding polypeptides are derived from Golden larch (*Pseudolarix amabilis*, Pinaceae). The polypeptide or the nucleic acid can be used in any of the method provided herein for producing a diterpenoid. Also provided herein are vectors and hosts containing the diTPS and that can be used for producing diterpenoids.

The diTPS to be used in methods provided herein also can be generated synthetically. Standard reference works setting forth the general principles of peptide synthesis technology and methods known to those of skill in the art include, for example: Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwood et al., Oxford University Press, Oxford, United Kingdom, 2000; Sambrook et al., Molecular Cloning: A Laboratory Manual, 3$^{rd}$ ed., Cold Spring Harbor Press, Cold Spring Harbor, N.Y. 2001; and Ausubel et al., Current Protocols in Molecular Biology, Greene Publishing Associates and John Wiley & Sons, N Y, 1994.

Also provided is a diTPS kit. The kit can contain one or more diTPS nucleic acid molecules. The kit can contain one or more diTPS polypeptides. The kit can contain a synthetic diTPS gene. The kit can contain a vector containing one or more diTPS nucleic acids. The kit can contain a host cell capable of expressing one or more than one diTPS polypeptide.

Isolation of Nucleic Acid Encoding Diterpene Synthases

The one or more than one polynucleotide sequences encoding the diTPS as provided herein can be prepared by any method known by the person skilled in the art. For example, the polynucleotide sequence encoding a diTPS can be amplified from a cDNA template, by polymerase chain reaction with specific primers. In such an example the codons of the cDNA can be chosen to favor the expression of said protein in the desired expression system. In other examples, nucleic acids encoding diterpene synthases, including any of the diTPS provided herein, can be cloned or isolated using any available methods known in the art for cloning and isolating nucleic acid molecules. Such methods include PCR amplification of nucleic acids and screening of libraries, including nucleic acid hybridization screening. In some examples, methods for amplification of nucleic acids can be used to isolate nucleic acid molecules encoding a diTPS polypeptide, including for example, polymerase chain reaction (PCR) methods. A nucleic acid containing material can be used as a starting material from which a diTPS-encoding nucleic acid molecule can be isolated. For example, DNA and mRNA preparations from Golden larch (*Pseudolarix amabilis*, Pinaceae), can be used to obtain diterpene synthase genes.

Nucleic acid libraries also can be used as a source of starting material. Primers can be designed to amplify a diterpene synthase-encoding molecule, such as a diTPS-encoding molecule. For example, primers can be designed based on known nucleic acid sequences encoding a diterpene synthase, such as a class I monofunctional diterpene synthase, such as set forth in SEQ ID NO.:2. Nucleic acid molecules generated by amplification can be sequenced and confirmed to encode a diTPS polypeptide.

Additional nucleotide sequences can be joined to a diTPS-encoding nucleic acid molecule, including linker sequences containing restriction endonuclease sites for the purpose of cloning the synthetic gene into a vector, for example, a protein expression vector or a vector designed for the amplification of the core protein coding DNA sequences. Furthermore, additional nucleotide sequences specifying functional DNA elements can be operatively linked to a diTPS-encoding nucleic acid molecule. Still further, nucleic acid encoding other moieties or domains also can be included so that the resulting synthase is a fusion protein. For example, nucleic acids encoding other enzymes, such as a GGPP synthase, or protein purification tags, such as His or Flag tags.

Vectors and Cells

The disclosure also relates, in part, to vectors containing such sequences, transformed cells, cell lines, and transgenic organisms. For recombinant expression of one or more of the diterpene synthase polypeptides provided herein, including diTPS polypeptides, the nucleic acid containing all or a portion of the nucleotide sequence encoding the synthase can be inserted into an appropriate expression vector, i.e., a vector that contains the necessary elements for the transcription and translation of the inserted protein coding sequence. Depending upon the expression system used, the necessary transcriptional and translational signals also can be supplied by the native promoter for a diTPS gene, and/or their flanking regions. For example, vectors containing a polynucleotide sequence encoding a diTPS are provided herein. The vector can be obtained and introduced in a host cell by well-known recombinant DNA and genetic engineering techniques. In some examples, a vector can contain the gene encoding a GGPP synthase, such as the gene encoding the GGPP synthase PxaTPS8 from Golden larch (*Pseudolarix amabilis*, Pinaceae) (SEQ ID NO:2).

The disclosure also provides a prokaryotic or eukaryotic host cell which is modified by a polynucleotide or a vector as provided herein. The host cell can be prokaryotic, such as bacterial, or eukaryotic, such as fungal (e.g., yeast), plant, archeae, insect, amphibian or animal cell. The host cell can contain a diTPS vector, a synthetic diTPS gene, and/or diTPS nucleic acid. The host cell can be any cell that is capable of being transformed by the vector, synthetic gene, and/or nucleic acid. The host cell can also be any cell that is capable of expressing the diTPS polypeptide. The host cell can be incubated under conditions that allow expression of the diTPS polypeptide.

Several of these organisms do not produce GGPP naturally. To be suitable to carry out the method of the invention, these organisms may need to be transformed with one or more sequences, such as a sequence encoding a GGPP synthase, that result in production of the precursor, GGPP. They can be so transformed either before the modification with the nucleic acid described according to any of the above embodiments, or simultaneously with a nucleotide sequence encoding diTPS, or a vector containing a nucleotide sequence encoding diTPS. Alternatively, in particular examples, the cells are yeast, such as *Saccharomyces cerevisiae*, that express an acyclic pyrophosphate terpene precursor, such as GGPP. The cells are used to produce a diterpene synthase, such as a diTPS polypeptide, by growing the above-described cells under conditions whereby the encoded diTPS is expressed by the cell. In some instances, the expressed synthase is purified. In other instances, the expressed synthase, such as a sibongilene synthase, converts GGPP to one or more terpenes (e.sibongilene) in the host cell.

Any method known to those of skill in the art for the insertion of DNA fragments into a vector can be used to construct expression vectors containing a chimeric gene containing appropriate transcriptional/translational control signals and protein coding sequences. These methods can include in vitro recombinant DNA and synthetic techniques and in vivo recombinants (genetic recombination). Expression of nucleic acid sequences encoding a diTPS polypeptide, or a fragment thereof, can be regulated by a second nucleic acid sequence so that the genes or fragments thereof are expressed in a host transformed with the recombinant DNA molecule(s). For example, expression of the proteins can be controlled by any promoter/enhancer known in the art. In a specific embodiment, the promoter is not native to the genes for a diTPS protein. Promoters that can be used include but are not limited to prokaryotic, yeast, mammalian and plant promoters. The type of promoter depends upon the expression system used, described in more detail below.

In a specific embodiment, a vector is used that contains a promoter operably linked to nucleic acids encoding a diTPS polypeptide, or a fragment thereof, thereof, one or more origins of replication, and optionally, one or more selectable markers (e.g., an antibiotic resistance gene). Vectors and systems for expression of diTPS polypeptides are described, including, for example, the pET28b(+) vector.

Expression Systems

Diterpene synthases, including diTPS polypeptides provided herein, can be produced by any methods known in the art for protein production including in vitro and in vivo methods such as, for example, the introduction of nucleic acid molecules encoding the diterpene synthase (e.g. sibongilene synthase) into a host cell or host plant for in vivo production or expression from nucleic acid molecules encoding the diterpene synthase (e.g. sibongilene synthase) in vitro. Diterpene synthases such as. sibongilene synthase polypeptides can be expressed in any organism suitable to produce the required amounts and forms of a synthase polypeptide. Expression hosts include prokaryotic and eukaryotic organisms such as *E. coli*, yeast, plants, insect cells, mammalian cells, including human cell lines and transgenic animals. Expression hosts can differ in their protein production levels as well as the types of post-translational modifications that are present on the expressed proteins. The choice of expression host can be made based on these and d other factors, such as regulatory and safety considerations, production costs and the need and methods for purification.

Isolated higher eukaryotic cells, for example cell culture, can also be used, instead of complete organisms, as hosts to carry out the method provided herein in vivo. Suitable eukaryotic cells can be any non-human cell, but are generally plant cells. Representative examples of a plant host cell include for example plants that naturally produce high amounts of terpenes. The plant can be selected from the family of Pinaceae, Funariacea, Solanaceae, Poaceae, Brassicaceae, Fabaceae, Malvaceae, Asteraceae or Lamiaceae. For example, the plant is selected from the genera *Picea* (spruce), *Pinus* (pine), *Abies* (fir), *Physcomitrella, Funariaceae, Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum, Nicotiana benthamiana* or *Physcomitrella patens*. Additional plants and plant cells include, for example, citrus, corn, rice, algae, and lemna. In other examples, the eukaryotic cells are yeast cells. Representative examples of a yeast host cell include those from the *Saccharomyces* genus (e.g. *Saccharomyces cerevisiae*) and *Pichia* genus (e.g. *Pichia pastoris*). In some examples, insect cells such as *Drosophila* cells and lepidopteran cells are used for the expression of a diTPS provided herein. Eukaryotic cells for expression also include mammalian cells lines such as Chinese hamster ovary (CHO) cells or baby hamster kidney (BHK) cells.

Eukaryotic expression hosts also include production in transgenic animals, for example, including production in serum, milk and eggs. There are several methods known in the art for the creation of transgenic host organisms or cells such as plants, fungi, prokaryotes, or cultures of higher eukaryotic cells. Appropriate cloning and expression vectors for use with bacterial, fungal, yeast, plant and mammalian cellular hosts are described, for example, in Pouwels et al., Cloning Vectors: A Laboratory Manual, 1985, Elsevier, New York and Sambrook et al., Molecular Cloning: A Laboratory Manual, 2$^{nd}$ edition, 1989, Cold Spring Harbor Laboratory Press. Cloning and expression vectors for higher plants and/or plant cells in particular are available to the skilled person. See for example Schardl et al. (1987) *Gene* 61: 1-11.

Methods for transforming host organisms or cells to harbor transgenic nucleic acids are familiar to the skilled person. For the creation of transgenic plants, for example, current methods include: electroporation of plant protoplasts, liposome-mediated transformation, *agrobacterium*-mediated transformation, polyethylene-glycol-mediated transformation, particle bombardment, microinjection of plant cells, and transformation using viruses.

Many expression vectors are available and known to those of skill in the art for the expression of a diterpene synthase, such as a diTPS provided herein. Exemplary of expression vectors are pET expression vectors, such as pET28b(+). The choice of expression vector is influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vectors in the cells.

Diterpene synthases, including diTPS polypeptides, also can be utilized or expressed as protein fusions. For example, a fusion can be generated to add additional functionality to a polypeptide. Examples of fusion proteins include, but are not limited to, fusions of a signal sequence, a tag such as for localization, e.g. a his6 tag or a myc tag, or a tag for purification, for example, a GST fusion, GFP fusion or CBP fusion, and a sequence for directing protein secretion and/or membrane association. In other examples, diterpene synthases such as diTPS polypeptides provided herein can be fused to GGPP synthase (see, e.g., Brodelius et al. (2002) *Eur. J Biochem.* 269:3570-3579).

Methods of production of diterpene synthase polypeptides, including sibongilene synthase polypeptides, can include co-expression of an acyclic pyrophosphate terpene precursor, such as GGPP, in the host cell. In some instances, the host cell naturally expresses GGPP. Such a cell can be modified to express greater quantities of GGPP (see e.g. U.S. Pat. Nos. 6,531,303, 6,689,593, 7,838,279 and 7,842,497). In other instances, a host cell that does not naturally produce GGPP is modified genetically to produce GGPP.

Prokaryotic Cells

Prokaryotes, especially *E. coli*, provide a system for producing large amounts of the diTPS polypeptides provided herein. Transformation of *E. coli* is a simple and rapid technique well known to those of skill in the art. Representative examples of a bacterial host cell include, but are not limited to, *E. coli* strains such as for example *E. coli* BL21DE3-C41 (Miroux and Walker (1996) *J Mol Biol* 260:289-298). Exemplary expression vectors for transformation of *E. coli* cells, include, for example, the pGEX expression vectors, the pQE expression vectors, and the pET expression vectors (see, U.S. Pat. No. 4,952,496; available from Novagen, Madison, Wis.; see, also literature published by Novagen describing the system). Such plasmids include pET11a, which contains the T7lac promoter, T7 terminator, the inducible *E. coli* lac operator, and the lac repressor gene; pET12a-c, which contains the T7 promoter, T7 terminator, and the *E. coli* ompT secretion signal; and pET15b and pET19b (Novagen, Madison, Wis.), which contain a His-Tag™ leader sequence for use in purification with a His column and a thrombin cleavage site that permits cleavage following purification over the column, the T7-lac promoter region and the T7 terminator; and pET28b (Novagen, Madison, Wis.), which contains a His-Tag™ leader sequence for use in purification with a His column and a thrombin cleavage site that permits cleavage following purification over the column, the T7-lac promoter region and the T7 terminator; and the pJET vectors (Thermo Scientific), such as the pJET1.2 vector which contains a lethal gene which is disrupted by ligation of a DNA insert into the cloning site and a T7 promoter for in vitro transcription.

Expression vectors for *E. coli* can contain inducible promoters that are useful for inducing high levels of protein expression and for expressing proteins that exhibit some toxicity to the host cells. Exemplary prokaryotic promoters include, for example, the β-lactamase promoter (Jay et al., (1981) *Proc. Natl. Acad. Sci. USA* 78:5543) and the tac promoter (DeBoer et al., (1983) *Proc. Natl. Acad. Sci. USA* 80:21-25); see also "Useful Proteins from Recombinant Bacteria": in Scientific American 242:79-94 (1980)). Examples of inducible promoters include the lac promoter, the trp promoter, the hybrid tac promoter, the T7 and SP6 RNA promoters and the temperature regulated $\lambda P_L$ promoter.

Diterpene synthases, including diTPS polypeptides provided herein can be expressed in the cytoplasmic environment of *E. coli*. The cytoplasm is a reducing environment and for some molecules, this can result in the formation of insoluble inclusion bodies. Reducing agents such as dithiothreitol and β-mercaptoethanol and denaturants (e.g., such as guanidine-HCl and urea) can be used to resolubilize the proteins. An alternative approach is the expression diTPS polypeptides in the periplasmic space of bacteria which provides an oxidizing environment and chaperonin-like and disulfide isomerases leading to the production of soluble protein. Typically, a leader sequence is fused to the protein to be expressed which directs the protein to the periplasm. The leader is then removed by signal peptidases inside the periplasm. Examples of periplasmic-targeting leader sequences include the pelB leader from the pectate lyase gene and the leader derived from the alkaline phosphatase gene. In some cases, periplasmic expression allows leakage of the expressed protein into the culture medium. The secretion of proteins allows quick and simple purification from the culture supernatant. Proteins that are not secreted can be obtained from the periplasm by osmotic lysis. Similar to cytoplasmic expression, in some cases proteins can become insoluble and denaturants and reducing agents can be used to facilitate solubilization and refolding. Temperature of induction and growth also can influence expression levels and solubility. Typically, temperatures between 25° C. and 37° C. are used. Mutations also can be used to increase solubility of expressed proteins. Typically, bacteria produce aglycosylated proteins.

Yeast Cells

Yeast systems, such as, but not limited to, those from the *Saccharomyces* genus (e.g. *Saccharomyces cerevisiae*), *Schizosaccharomyces pombe, Yarrowia lipolytica, Kluyveromyces lactis*, and *Pichia pastoris* can be used to express the diterpene synthases, such as the diTPS polypeptides, provided herein. Yeast expression systems also can be used to produce diterpenes whose reactions are catalyzed by the synthases. Yeast can be transformed with episomal replicating vectors or by stable chromosomal integration by homologous recombination. In some examples, inducible promoters are used to regulate gene expression. Exemplary promoter sequences for expression of diTPS polypeptides in yeast include, among others, promoters for metallothionine, 3-phosphoglycerate kinase (Hitzeman et al. (1980) *J Biol. Chem.* 255:2073), or other glycolytic enzymes (Hess et al. (1968) *J Adv. Enzyme Reg.* 7:149; and Holland et al. (1978) *Biochem.* 17:4900), such as enolase, glyceraldehyde phosphate dehydrogenase, hexokinase, pyruvate decarboxylase, phosphofructokinase, glucose phosphate isomerase, 3-phosphoglycerate mutase, pyruvate kinase, triosephosphate isomerase, phosphoglucose isomerase, and glucokinase.

Other suitable vectors and promoters for use in yeast expression are further described in Hitzeman, EPA-73,657 or in Fleer et al. (1991) *Gene*, 107:285-195; and van den Berg et al. (1990) *Bio/Technology*, 8:135-139. Another alternative includes, but is not limited to, the glucose-repressible ADH2 promoter described by Russell et al. (*J. Biol. Chem.* 258:2674, 1982) and Beier et al. (*Nature* 300:724, 1982), or a modified ADH1 promoter. Shuttle vectors replicable in yeast and *E. coli* can be constructed by, for example, inserting DNA sequences from pBR322 for selection and replication in *E. coli* ($Amp^r$ gene and origin of replication) into a yeast vector.

Yeast expression vectors can include a selectable marker such as LEU2, TRP1, HIS3, and URA3 for selection and maintenance of the transformed DNA. Proteins expressed in yeast are often soluble and co-expression with chaperonins, such as Bip and protein disulfide isomerase, can improve expression levels and solubility. Additionally, proteins expressed in yeast can be directed for secretion using secretion signal peptide fusions such as the yeast mating type alpha-factor secretion signal from *Saccharomyces cerevisiae* and fusions with yeast cell surface proteins such as the Aga2p mating adhesion receptor or the *Arxula adeninivorans* glucoamylase. A protease cleavage site (e.g., the Kex-2 protease) can be engineered to remove the fused sequences from the polypeptides as they exit the secretion pathway.

Yeast naturally express the required proteins, including GGPP synthase (BST1; which can produce GGPP) for the mevalonate-dependent isoprenoid biosynthetic pathway. Thus, expression of the diterpene synthases, including diTPS polypeptides provided herein, in yeast cells can result in the production of diterpenes, such as sibongilene from GGPP. Exemplary yeast cells for the expression of terpene synthases, including diTPS polypeptides, include yeast modified to express increased levels of FPP and/or GGPP. For example, yeast cells can be modified to produce less squalene synthase or less active squalene synthase (e.g. erg9 mutants; see e.g. U.S. Pat. Nos. 6,531,303 and 6,689,593). This results in accumulation of FPP in the host cell at higher levels compared to wild type yeast cells, which in turn can result in increased yields of GGPP and diterpenes (e.g. sibongilene, pseudolaric acid A, pseudolaric acid B, pseudolaric acid C, or a derivative thereof). In another example, yeast cells can be modified to produce more GGPP synthase by introduction of a GGPP synthase gene, such as BTS1 from *S. cerevisiae*, crtE from *Erwinia uredovora*, crtE from *Xanthophyllomyces dendrorhous*, al-3 from *Neuspora crassa* or ggs from *Giverella fujiuroi* (see U.S. Pat. No. 7,842,497). In some examples, the native GGPP gene in such yeast can be deleted. Other modifications that enable increased production of GGPP in yeast include, for example, but are not limited to, modifications that increase production of acetyl CoA, inactivate genes that encode enzymes that use FPP and GPP as substrate and overexpress of HMG-CoA reductases, as described in U.S. Pat. No. 7,842,497. Exemplary modified yeast cells include, but are not limited to, modified *Saccharomyces cerevisiae* strains CALI5-1 (ura3, leu2, his3, trp1, Δ erg9::HIS3, HMG2cat/TRP1::rDNA, dpp1, sue), ALX7-95 (ura3, his3, trp1, Aerg9::HIS3, HMG2cat/TRP1::rDNA, dpp1 sue), ALX11-30 (ura3, trp1, erg9$^{def}$25, HMG2cat/TRP1::rDNA, dpp1, sue), which are known and described in one or more of U.S. Pat. Nos. 6,531,303, 6,689,593, 7,838,279, 7,842,497, and published U.S. Pat. Application Serial Nos. 20040249219 and 20110189717.

Plants and Plant Cells

Transgenic plant cells and plants can be used for the expression of diterpene synthases, including diTPS polypeptides provided herein. Expression constructs are typically transferred to plants using direct DNA transfer such as microprojectile bombardment and PEG-mediated transfer into protoplasts, and with *agrobacterium*-mediated transformation. Expression vectors can include promoter and enhancer sequences, transcriptional termination elements, and translational control elements. Expression vectors and transformation techniques are usually divided between dicot hosts, such as *Arabidopsis* and tobacco, and monocot hosts, such as corn and rice. Examples of plant promoters used for expression include the cauliflower mosaic virus promoter, the nopaline synthase promoter, the ribose bisphosphate carboxylase promoter and the ubiquitin and UBQ3 promoters. Selectable markers such as hygromycin, phosphomannose isomerase and neomycin phosphotransferase are often used to facilitate selection and maintenance of transformed cells. Transformed plant cells can be maintained in culture as cells, aggregates (callus tissue) or regenerated into whole plants. Transgenic plant cells also can include algae engineered to produce proteins (see, for example, Mayfield et al. (2003) *Proc Natl Acad Sci USA* 100:438-442). Transformed plants include, for example, plants selected from the genera *Picea* (spruce), *Pinus* (pine), *Abies* (fir), *Physcomitrella, Funariaceae, Nicotiana, Solanum, Sorghum, Arabidopsis, Medicago* (alfalfa), *Gossypium* (cotton), *Brassica* (rape), *Artemisia, Salvia* and *Mentha*. In some examples, the plant belongs to the species of *Nicotiana tabacum, Nicotiana benthamiana* or *Physcomitrella patens*, and is transformed with vectors that overexpress a diTPS and optionally a geranylgeranyl diphosphate synthase, such as described in U.S. Pat. Pub. No. 20090123984 and U.S. Pat. No. 7,906,710.

Insects and Insect Cells

Insects and insect cells, particularly a baculovirus expression system, can be used for expressing diterpene synthases, including diTPS polypeptides provided herein (see, for example, Muneta et al. (2003) *J Vet. Med. Sci.* 65(2):219-223). Insect cells and insect larvae, including expression in the haemolymph, express high levels of protein and are capable of most of the post-translational modifications used by higher eukaryotes. Baculoviruses have a restrictive host range which improves the safety and reduces regulatory concerns of eukaryotic expression. Typically, expression vectors use a promoter such as the polyhedrin promoter of baculovirus for high level expression. Commonly used baculovirus systems include baculoviruses such as *Autographa californica* nuclear polyhedrosis virus (AcNPV), and the *Bombyx mori* nuclear polyhedrosis virus (BmNPV) and an insect cell line such as Sf9 derived from *Spodoptera frugiperda*, *Pseudaletia unipuncta* (A7S) and *Danaus plexippus* (DpN1). For high level expression, the nucleotide sequence of the molecule to be expressed is fused immediately downstream of the polyhedrin initiation codon of the virus. Mammalian secretion signals are accurately processed in insect cells and can be used to secrete the expressed protein into the culture medium. In addition, the cell lines *Pseudaletia unipuncta* (A7S) and *Danaus plexippus* (DpN1) produce proteins with glycosylation patterns similar to mammalian cell systems.

An alternative expression system in insect cells is the use of stably transformed cells. Cell lines such as the Schnieder 2 (S2) and Kc cells (*Drosophila melanogaster*) and C7 cells (*Aedes albopictus*) can be used for expression. The *Drosophila* metallothionein promoter can be used to induce high levels of expression in the presence of heavy metal induction with cadmium or copper. Expression vectors are typically maintained by the use of selectable markers such as neomycin and hygromycin.

Mammalian Expression

Mammalian expression systems can be used to express diterpene synthases, including diTPS polypeptides provided herein and also can be used to produce diterpenes whose reactions are catalyzed by the synthases. Expression constructs can be transferred to mammalian cells by viral infection such as adenovirus or by direct DNA transfer such as liposomes, calcium phosphate, DEAE-dextran and by physical means such as electroporation and microinjection. Expression vectors for mammalian cells typically include an mRNA cap site, a TATA box, a translational initiation sequence (Kozak consensus sequence) and polyadenylation elements. Such vectors often include transcriptional promoter-enhancers for high level expression, for example the SV40 promoter-enhancer, the human cytomegalovirus (CMV) promoter, and the long terminal repeat of Rous sarcoma virus (RSV). These promoter-enhancers are active in many cell types. Tissue and cell-type promoters and enhancer regions also can be used for expression. Exemplary promoter/enhancer regions include, but are not limited to, those from genes such as elastase I, insulin, immunoglobulin, mouse mammary tumor virus, albumin, alpha-fetoprotein, alpha 1-antitrypsin, beta-globin, myelin basic protein, myosin light chain-2 and gonadotropic releasing hormone gene control. Selectable markers can be used to select for and maintain cells with the expression construct. Examples of selectable marker genes include, but are not limited to, hygromycin B phosphotransferase, adenosine deaminase, xanthine-guanine phosphoribosyl transferase, aminoglycoside phosphotransferase, dihydrofolate reductase and thymidine kinase. Fusion with cell surface signaling molecules such as TCR-ζ and Fc$_\varepsilon$RI-γ can direct expression of the proteins in an active state on the cell surface.

Many cell lines are available for mammalian expression including mouse, rat human, monkey, and chicken and hamster cells. Exemplary cell lines include, but are not limited to, BHK (i.e. BHK-21 cells), 293-F, CHO, CHO Express (CHOX; Excellgene), Balb/3T3, HeLa, MT2, mouse NSO (non-secreting) and other myeloma cell lines, hybridoma and heterohybridoma cell lines, lymphocytes, fibroblasts, Sp2/0, COS, NIH3T3, HEK293, 293S, 293T, 2B8, and HKB cells. Cell lines also are available adapted to serum-free media which facilitates purification of secreted proteins from the cell culture media. One such example is the serum free EBNA-1 cell line (Pham et al. (2003) *Biotechnol. Bioeng.* 84:332-342).

Purification

Also provided is a method of producing the diTPS polypeptide. The diTPS polypeptide can be purified using standard chromatographic techniques.

The polypeptide to be used when the method is carried out in vitro can be obtained by extraction from any organism expressing it, using standard protein or enzyme extraction technologies. If the host organism is a unicellular organism or cell releasing the polypeptide of the invention into the culture medium, the polypeptide can simply be collected from the culture medium, for example by centrifugation, optionally followed by washing steps and re-suspension in suitable buffer solutions. If the organism or cell accumulates the polypeptide within its cells, the polypeptide can be obtained by disruption or lysis of the cells and further extraction of the polypeptide from the cell lysate.

Methods for purification of diterpene synthases, such as diTPS polypeptides, from host cells depend on the chosen host cells and expression systems. For secreted molecules, proteins are generally purified from the culture media after removing the cells. For intracellular expression, cells can be lysed and the proteins purified from the extract. When transgenic organisms such as transgenic plants and animals are used for expression, tissues or organs can be used as starting material to make a lysed cell extract. Additionally, transgenic animal production can include the production of polypeptides in milk or eggs, which can be collected, and if necessary the proteins can be extracted and further purified using standard methods in the art.

Diterpene synthases, including diTPS polypeptides provided herein, can be purified using standard protein purification techniques known in the art including but not limited to, SDS-PAGE, size fraction and size exclusion chromatography, ammonium sulfate precipitation, chelate chromatography and ionic exchange chromatography. Expression constructs also can be engineered to add an affinity tag such as a myc epitope, GST fusion or His6 and affinity purified with myc antibody, glutathione resin, and Ni-resin, respectively, to a protein. Purity can be assessed by any method known in the art including gel electrophoresis and staining and spectrophotometric techniques. The polypeptides, either in an isolated form or together with other proteins, for example in a crude protein extract obtained from cultured cells or microorganisms, can then be suspended in a buffer solution at optimal pH. If adequate, salts, DTT, BSA and other kinds of enzymatic co-factors, can be added in order to optimize enzyme activity.

Fusion Proteins

Fusion proteins containing a diterpene synthase, including diTPS polypeptides, and one or more other polypeptides also are provided. Linkage of a diterpene synthase polypeptide with another polypeptide can be effected directly or indirectly via a linker. In one example, linkage can be by chemical linkage, such as via heterobifunctional agents or thiol linkages or other such linkages. Fusion also can be effected by recombinant means. Fusion of a diterpene synthase, such as a diTPS polypeptide, e.g., a sibongilene synthase, to another polypeptide can be to the N- or C-terminus of the diTPS polypeptide.

A fusion protein can be produced by standard recombinant techniques. For example, DNA fragments coding for the different polypeptide sequences can be ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel et al. (eds.) Current Protocols in Molecular Biology, John Wiley & Sons, 1992). Moreover, many expression vectors are commercially available that already encode a fusion moiety (e.g., a GST polypeptide). For example, an PxaTPS8 polypeptide-encoding nucleic acid can be cloned into such an expression vector such that nucleic acid encoding PxaTPS8 is linked in-frame to a polypeptide encoding a protein purification tag, such as a His tag. In another example, a nucleic acid molecule encoding a diTPS polypeptide can be linked in-frame to a polypeptide encoding a GGPP synthase. The diTPS polypeptide and additional polypeptide can be linked directly, without a linker, or alternatively, linked indirectly in-frame with a linker.

III. Formulations

The compositions of the present invention can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and the anti-inflammatory glucocorticosteroid and/or the GR modulator of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the anti-inflammatory glucocorticosteroid and/or the GR modulator of Formula I.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the anti-inflammatory glucocorticosteroid and/or the GR modulator of Formula I mixed with a filler or binders such as lactose or starches, lubricants such as talc or magnesium stearate, and, optionally, stabilizers. In soft capsules, the anti-inflammatory glucocorticosteroid and/or the GR modulator of Formula I may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the anti-inflammatory glucocorticosteroid and/or the GR modulator of Formula I are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the anti-inflammatory glucocorticosteroid and/or the GR modulator of Formula I in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the anti-inflammatory glucocorticosteroid and/or the GR modulator of Formula I in a vegetable oil, such as *arachis* oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, *J. Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Gene discovery and cDNA cloning. The root-specific transcriptome of *P. amabilis* was described previously (11). Transcripts of interest were selected by querying the transcriptomes against a curated TPS database and subsequent phylogenetic analysis. Relative transcript abundance was calculated by mapping adapter-trimmed Illumina reads against the assembled transcripts using BWA version 0.5.9-r16. Reads were mapped as paired with 350 bp maximum insert size. Selected cDNAs were amplified from total RNA with gene-specific oligonucleotides (Table 3) and ligated into the pJET vector (www.Clontech.com) for sequence verification.

TABLE 3

Oligonucleotides used in this study

| Designation | Gene | Sequence (5'-3') | SEQ ID NO: |
|---|---|---|---|
| pET28b(+) | PxaTPS5-Forward | TATCATATGGCTGGCGTTTCTGTTG | 7 |
| | PxaTPS5-Reverse | TATGTCGACTTAAAGTGGGAGCGGATCA | 8 |
| | PxaTPS8-Forward | TATCATATGATACGGTCAAATACTTCG | 9 |
| | PxaTPS8-Reverse | TGAGAGCTCTCATAAAGACACAGCTTG | 10 |
| pET28b(+) PxaTPS8 variants | R558A-sense | CCACGTTTCTATGTGCAGTGAACCTC | 11 |
| | R558A-AS | GAGGTTCACTGCACATAGAAACGTGG | 12 |
| | S696I-sense | ATGTAAACCAATCGTGACCTTGCTGTTC | 13 |
| | S696I-antisense | GAACAGCAAGGTCACGATTGGTTTACAT | 14 |
| | S696V-sense | CTATATGTAAACCAACCGTGACCTTGCTGT | 15 |
| | S696V-antisense | ACAGCAAGGTCACGGTTGGTTTACATATAG | 16 |
| | G697S-sense | ATCGCTATATGTAAACTACTCGTGACCTTGCTG | 17 |
| | G697S-antisense | CAGCAAGGTCACGAGTAGTTTACATATAGCGAT | 18 |
| | Y564T-sense | CCATAGTGTAAGTTTCCACGTTTC | 19 |
| | Y564T-antisense | GAAACGTGGAAACTTACACTATGG | 20 |
| | Y564V-sense | CCATAGTGTAAACTTCCACGTTTC | 21 |
| | Y564V-antisense | GAAACGTGGAAGTTTACACTATGG | 22 |
| | Y564F-sense | CCATAGTGTAAAATTCCACGTTTC | 23 |
| | Y564F-antisense | GAAACGTGGAATTTTACACTATGG | 24 |
| | A701C-sense | GTGAGGATGGGCAATATACATATATGTAAACCAC | 25 |
| | A701C-antisense | GTGGTTTACATATATGTATATTGCCCATCCTCAC | 26 |
| | A701L-sense | GATGGGCAATATCAGTATATGTAAACCACTCG | 27 |
| | A701L-AS | CGAGTGGTTTACATATACTGATATTGCCCATC | 28 |
| pLIFE33 | PxaTPS5-Forward | GGCTTAAUAATGGCTGGCGTTTCTGTTG | 29 |
| | PxaTPS5-Reverse | GGTTTAAUTTAAAGTGGGAGCGGATCAATTAGAC | 30 |
| | PxaTPS8-Forward | GGCTTAAUAATGTCAAGATTTACATCTGCTGC | 31 |
| | PxaTPS8-Reverse | GGTTTAAUTTATAAAGACACAGCTTGAACGAG | 32 |
| pESC-His | PxaTPS8-Forward | GAATTCAACCCTCACTAAAGGGCGGCCGCATGACGAAAAGGAGTGAAGCAGATG | 33 |
| | PxaTPS8-Reverse | CTTGTAATCCATCGATACTAGTGCGGCCGCTTATAAAGACACAGCTTGAACGAGAGTTC | 34 |

EXAMPLES

Example 1: Discovery and Characterization of Novel Diterpene Synthase

Materials and Methods

Plant material. One-year-old *P. amabilis* saplings were obtained from the *Camellia* Forest nursery (www.camforest.com). Seeds of *Nicotiana benthamiana* were collected from mature plants. Plants were grown in Conviron TCR120 growth chambers (www.conviron.com) under a photoperiod of 16 h, 60% relative humidity, 100 μmol m$^{-2}$ s$^{-1}$ light intensity, and a day/night temperature cycle of 21/18° C.

In vitro enzyme analysis. A truncated form, lacking the plastidial transit peptide, of PxaTPS8 (Δ76) and the full length PxaTPS5 cDNA were subcloned into the pET28b vector (www.emdmillipore.com) and expressed in *E. coli* BL21DE3-C41 cells, followed by Ni$^{2+}$-affinity purification and enzyme assays as previously described (11). For activity assays, 50 μg of recombinant protein and 15 μM of GPP, FPP or GGPP (www.sigma.com) were mixed in 50 mM HEPES (pH 7.2), 7.5 mM MgCl2, 5% (v/v) glycerol, 5 mM DTT, and incubated at 30° C. for 1 h. Product were extracted with 500 μl pentane analyzed by GC/MS.

Expression in *Nicotiana benthamiana*. Full-length constructs of PxaTPS5 and PxaTPS8 were cloned into the pLIFE33 vector and transformed into *A. tumefaciens* strain GV3101 as previously described (11). Cultures containing the PxaTPS8 or PxaTPS5 constructs were mixed with one culture volume of the RNA silencing suppressor construct p19 (42), and pressure infiltrated into the abaxial side of the leaves of 6-week-old *N. benthamiana* plants. Expression of p19 only served as a control. After five days, metabolites were extracted from a single infected leaf and analyzed by GC/MS.

Sibongilene formation in yeast. The truncated PxaTPS8 (Δ76) was cloned into multiple cloning site 1 of the pESC-HIS:BTS1 plasmid for co-expression with the yeast endogenous GGPP synthase BTS1 (34). Plasmids were transformed into the *S. cerevisiae* strain AM94 (35) and cells grown in 1 L selective dropout medium (-His, -Leu, with 2% dextrose) at 30° C. and 250 rpm until an $OD_{600}$ of ~0.6. Cells were transferred into 1 L of YEP medium with 2% galactose for induction. After 41 h, the diterpene product was extracted from harvested cells by vortexing with glass beads in 5 ml of diethyl ether and separation on a silica matrix using 95:5% hexane:ethyl acetate (v,v).

GC/MS analysis. Terpenes were analyzed on an Agilent 7890B GC interfaced with a 5977 Extractor XL MSD at 70 eV and 1.2 ml $min^{-1}$ He flow, using a HP5-ms column (30 m, 250 µm i.d., 0.25 µm film). GC parameters: 40-50° C. for 1-2 min, 10-20° C. $min^{-1}$ to 300° C., hold 3 min; pulsed splitless injection at 250° C.

NMR analysis. Sibongilene was produced for NMR analysis using an *E. coli* system engineered for terpene formation (28). PxaTPS8 expression was conducted in 2 L Terrific Broth (TB, pH 7.0) medium at 16° C., and induction with 1 mM IPTG and 2 mM MgCl2. After 72 h, the sibongilene was extracted with 1 L hexane and purified on silica matrix (70-230 mesh size) using hexane. Proton, $^{13}C$ and HSQC spectra were acquired in deuterated chloroform on a Bruker 800 MHz Avance III spectrometer equipped with a Bruker 5 mm CPTCI cryoprobe.

Quantum chemical calculations. NMR calculations were performed with Gaussian 09 using the B3LYP method (43-47). Single point energies and molecular geometries were calculated using the 6-31+G(d,p) basis set. Initial conformational searches were completed using Spartan 10 (48) and the Merck Molecular Force Field (MMFF94) (49). NMR shielding tensors were calculated with the Gauge-Independent Atomic Orbital (GIAO) method, with a 6-311+g(2d,p) basis set and the SMD continuum solvent model (50) for chloroform. Scaling factors for chemical shift predictions derive from the Chemical Shift Repository (cheshirenmr.info) and used as described there. Probable correctness of the structure assignment was assesses via DP4 analysis (31). Mechanistic calculations were carried out at the mPW1PW91/6-31+G(d,p)/B3LYP/6-31+G(d,p) level (44-47,51) validated for carbocation reactions (29,32,37). Intrinsic reaction coordinate (IRC) calculations (52) verified the observed transition state structure to be connected to A and B. Structures were visualized in CYLview (www.cylview.org). This report is part 13 of our series on computational studies on diterpene-forming carbocation rearrangements (for part 12 see reference 53).

Phylogenetic analysis. Protein sequence alignments were performed using clustalW2 and curated with Gblocks (54). A maximum likelihood phylogenetic tree was generated in PhyML (55) with 1000 bootstrap repetitions. Abbreviations and accession numbers for proteins used in the phylogenetic analysis are provided in Table 2.

TABLE 2

Diterpene synthases used for phylogenetic analyses

| Abbreviation | Protein | Accession No. |
|---|---|---|
| AbCAS | Cis-abienol synthase, *Abies balsamea* | JN254808 |
| AbISO | Isopimaradiene synthase, *Abies balsamea* | JN254806 |
| AbLAS | Levopimaradiene/abietadiene synthase, *Abies balsamea* | JN254805 |
| AgAS | Abietadiene synthase, *Abies grandis* | AAK83563 |
| AgBIS | E-α-Bisabolene synthase, *Abies grandis* | AF006195 |
| AgCAM | Camphene synthase, *Abies grandis* | AAB70707 |
| AgHUM | γ-Humulene synthase, *Abies grandis* | AAC05728 |
| AgLIM | 4S-Limonene synthase, *Abies grandis* | AAB70907 |
| AgSEL | δ-Selinene synthase, *Abies grandis* | AAC05727 |
| AgTOL | Terpinolene synthase, *Abies grandis* | AAF61454 |
| GbLS | Levopimaradiene synthase, *Ginkgo biloba* | AAS89668 |
| PaBIS | E-α-bisabolene synthase, *Picea abies* | AY473619 |
| PaFAR | α-Farnesene synthase, *Picea abies* | AAS47697 |
| PaISO | Isopimaradiene synthase, *Picea abies* | AY473620 |
| PaLAS | Levopimaradiene/abietadiene synthase, *Picea abies* | AAS47691 |
| PaLIM | Limonene synthase, *Picea abies* | AAS47694 |
| PaLIN | (−)-Linalool synthase, *Picea abies* | AAS47693 |
| PaLON | Longifolene synthase, *Picea abies* | AAS47695 |
| PaMYR | Myrcene synthase, *Picea abies* | AAS47696 |
| PaPIN | α/β-Pinene synthase, *Picea abies* | AAS47692 |
| PbaISO | Isopimaradiene synthase, *Pinus banksiana* | M4HXW5 |
| PbaLAS | Levopimaradiene/abietadiene synthase, *Pinus banksiana* | M4HXU6 |
| PbaPIM | Pimaradiene synthase, *Pinus banksiana* | M4HY08 |
| PcISO | Isopimaradiene synthase, *Pinus contorta* | JQ240314 |
| PcLAS | Levopimaradiene/abietadiene synthase, *Pinus contorta* | JQ240310 |
| PcPIM | Pimaradiene synthase, *Pinus contorta* | JQ240315 |
| PgCAR | 3-Carene synthase, *Picea glauca* | ADZ45510 |
| PgCIN | 1,8-Cineole synthase, *Picea glauca* | ADZ45498 |
| PgLIN | (−)-Linalool synthase, *Picea glauca* | ADZ45500 |
| PmBIS | E-γ-Bisabolene synthase, *Pseudotsuga menziesii* | AAX07266 |
| PmFAR | β-Farnesene synthase, *Pseudotsuga menziesii* | AAX07265 |
| PmTOL | Terpinolene synthase, *Pseudotsuga menziesii* | AAX07264 |
| PpCPSKS | Ent-kaurene/kaurenol synthase, *Physcomitrella patens* | BAF61135 |
| PsiCAR | 3-Carene synthase, *Picea sitchensis* | ADU85924 |
| PsiISO | Isopimaradiene synthase, *Picea sitchensis* | ADZ45512 |
| PsiLAS | Levopimaradiene/abietadiene synthase, *Picea sitchensis* | ADZ45517 |
| PsiLON | Longipinene synthase, *Picea sitchensis* | ADZ45516 |

TABLE 2-continued

Diterpene synthases used for phylogenetic analyses

| Abbreviation | Protein | Accession No. |
|---|---|---|
| PsiPHE | β-Phellandrene synthase, *Picea sitchensis* | ADZ45506 |
| PsiSAB | Sabinene synthase, *Picea sitchensis* | ADU85929 |
| PsyCARY | β-Caryophyllene synthase, *Pinus sylvestris* | B4XAK4 |
| PtFAR | α-Farnesene synthase, *Pinus taeda* | AAO61226 |
| PtTOL | α-Terpineol synthase, *Pinus taeda* | Q84KL4 |
| PxaTPS4 | Levopimaradiene/abietadiene synthase, *Pseudolarix amabilis* | AGN70885 |
| TbaTXS | Taxadiene synthase, *Taxus baccata* | AAR02861 |
| TbrTXS | Taxadiene synthase, *Taxus brevifolia* | U48796 |
| TcTXS | Taxadiene synthase, *Taxus cuspidata* | DQ305407 |
| TxmTXS | Taxadiene synthase, *Taxus* x *media* | AAS18603 |

Homology modeling and site-directed mutagenesis. Homology models of PxaTPS5 and PxaTPS8 were generated using SWISS-MODEL based on the crystal structure of *Abies grandis* α-bisabolene synthase (24, 3EAS) with stereochemical validation using Ramachandran plots. GGPP was docked in the active site using Molegro Virtual Docker (56). Protein variants were generated using site-specific sense and anti-sense oligonucleotides (Table 3) and the pET28b:PxaTPS8 construct as template. DpnI treatment removed template plasmids. All protein variants were sequence verified prior to analysis.

Accession numbers. Nucleotide sequences described in this study have been deposited to the National Center for Biotechnology Information (NCBI) GenBank™/EBI Data Bank with the following accession numbers: PxaTPS8 (KU685114) and PxaTPS5 (KU685114).

Results

TPS in the golden larch root transcriptome. Pseudolaric acids are almost exclusively found in the roots of golden larch (5). We had previously developed a root-specific transcriptome resource (11), in which we found a total of 16 candidate TPS genes (FIG. 1). Of the five diTPSs (PxaTPS4, 10, 12, 15 and 16), with highest database matches to known diTPSs, four represented partial sequences putatively annotated as ent-kaurene synthase or class I/II diTPSs. The full length class I/II diTPS PxaTPS4 was biochemically confirmed as a levopimaradiene/abietadiene synthase (11).

None of the identified diTPS candidates matched the predicted class I diTPS hypothesized to be involved in PAB biosynthesis. We therefore investigated the remaining TPSs, whose top database matches were either mono- or sesqui-TPSs. The sequences of four transcripts (PxaTPS5-8) of particular interest resembled most closely 3-domain gymnosperm E-α-bisabolene synthases (BISs), a sesqui-TPS. Of these, PxaTPS8 was given priority for further characterization, due to its high transcript abundance in roots as identified by RNAseq-based transcript mapping (FIG. 1).

Figure 2:
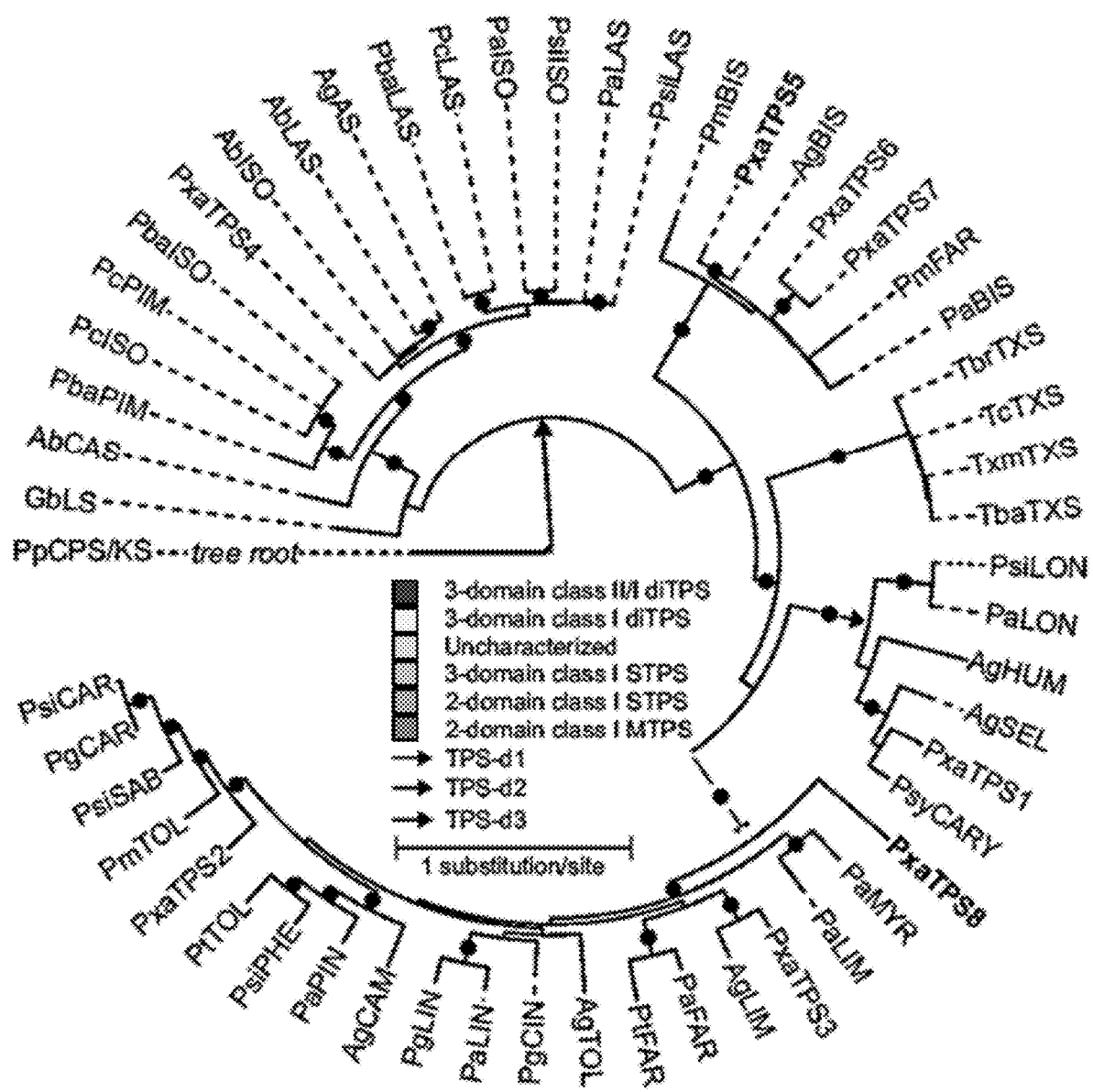
FIG. 2. Maximum likelihood tree illustrating the phylogenetic relationship of PxaTPS8 with members of the gymnosperm TPS-d clade. Bootstrap support of >80% (1000 repetitions) is highlighted. Tree rooted with *Physcomitrella patens* ent-kaurene synthase. Abbreviations and accession numbers are detailed in Table 2.

Sequence phylogeny places the 3-domain PxaTPS8 into an unusual position of the gymnosperm TPS family. The four BIS-like candidates identified in the golden larch root transcriptome resembled typical 3-domain class I TPSs, lacking a class II active site and featuring the DDxxD and NSE/DTE class I catalytic motifs (24). A 3-domain structure is typical for gymnosperm TPSs of the TPS-d3 Clade. As expected, our sequence phylogeny placed golden larch PxaTPS5, 6 and 7 closely with known BISs from grand fir (*Abies grandis*), Douglas fir (*Pseudotsuga menziesii*), and Norway spruce (*Picea abies*) within the gymnosperm TPS-d3 Clade (FIG. 2). Surprisingly, despite its 3-domain architecture, PxaTPS8 emerged outside the TPS-d3 Clade as a distant branch at the base of the TPS-dl Clade, which contains known 2-domain mono- and sesqui-TPSs. Phylogenetic position of a 3-domain TPS with the TPS-dl Clade is unprecedented, and suggested an unusual evolutionary path of sequence divergence leading to PxaTPS8 in golden larch. The unusual pairing of a 3-domain structure and TPS-dl Clade association prohibited a functional prediction of PxaTPS8 based on similarity with any known gymnosperm mono-, sesqui- or diTPS. However, these features also made it a prime candidate for a potentially unusual function.

Figure 3A:
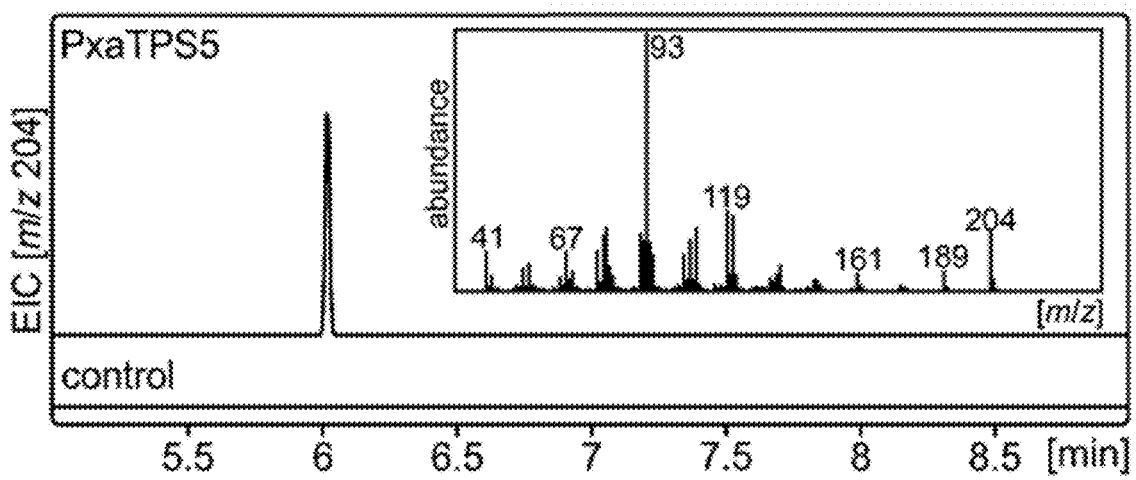
FIGS. 3A-3C Functional characterization of PxaTPS5 and PxaTPS8. GC/MS analysis of products resulting from *Agrobacterium*-mediated transient expression of PxaTPS5 [FIG. 3A] and PxaTPS8 [FIG. 3B] in *Nicotiana benthamiana*. Controls represent expression of the silencing suppressor protein p19 alone. Results are depicted as individual spectra.
Figure 3B:
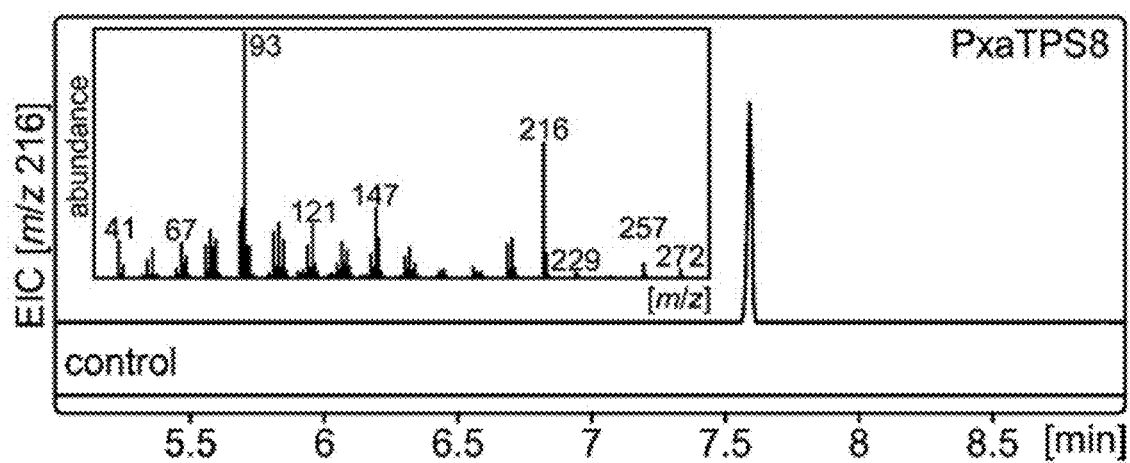
Figure 7A:
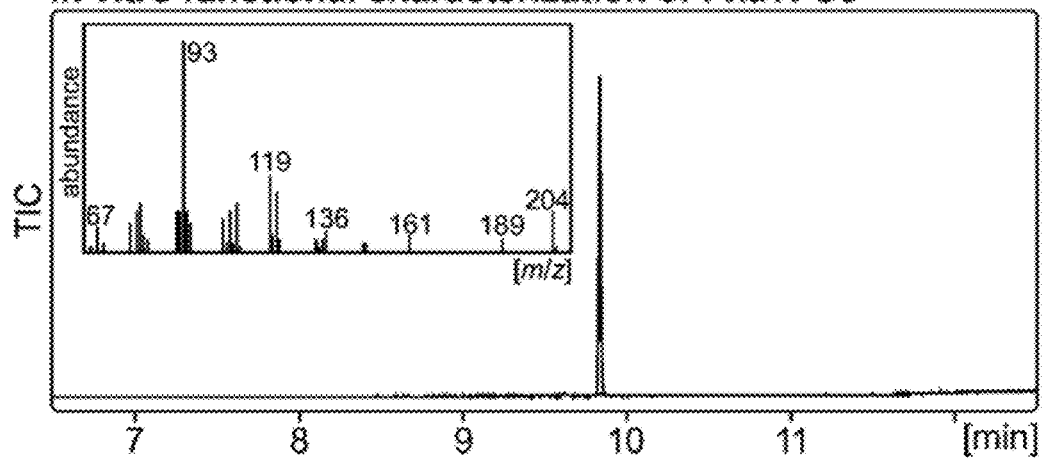
FIGS. 7A-7C Illustrates data produced by in vitro functional assays of PxaTPS5 and PxaTPS8. GC-MS analysis of reaction products obtained from in vitro enzyme assays of recombinant PxaTPS5 with farnesyl diphosphate (FPP) as a substrate [FIG. 7A], and PxaTPS8 with GGPP as a substrate [FIG. 7B].
Figure 7B:
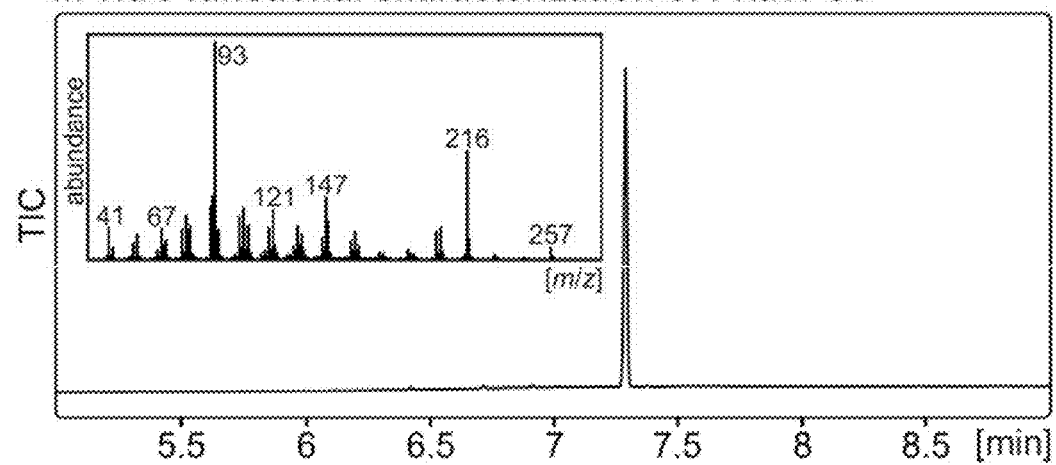
Figure 7C:
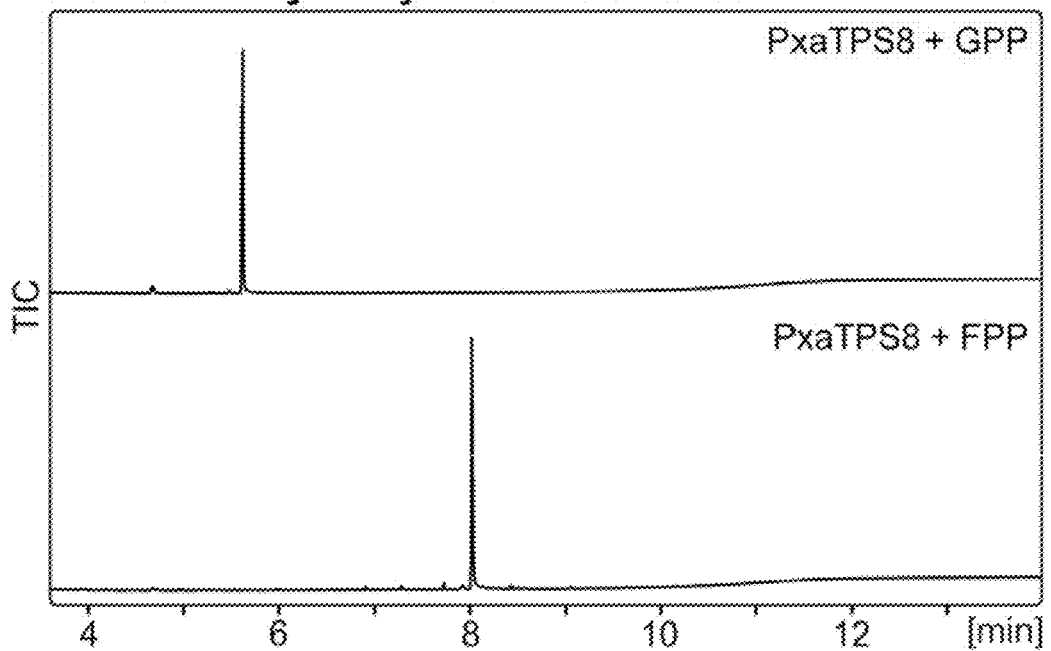

PxaTPS8 produces a novel diterpene. We performed in vitro enzyme assays with PxaTPS8 expressed in *E. coli* and in vivo assays using transient *Agrobacterium*-mediated expression in *Nicotiana benthamiana*. For comparison we also functionally characterized PxaTPS5, which represents a TPS-d3 BIS-like enzyme (FIG. 2). In vivo activity assays verified PxaTPS5 as an α-BIS, as based on comparison to product reference mass spectra of known α-BISs from grand fir and Norway spruce (20,27) (FIG. 3A). In contrast, in vivo assays of PxaTPS8 revealed as a single product a previously unknown diterpene with a fragmentation pattern featuring dominant ions of m/z 93(100), 121(25), 147(31), and 216 (57) (FIG. 3B). In vitro assays using affinity-purified recombinant proteins confirmed the activity of PxaTPS5 and PxaTPS8 (FIG. 7). PxaTPS8 was active only with GGPP as a substrate, while no product formation was detected in assays with geranyl diphosphate (GPP) or farnesyl diphosphate (FPP) (FIG. 7).

Figure 3C:
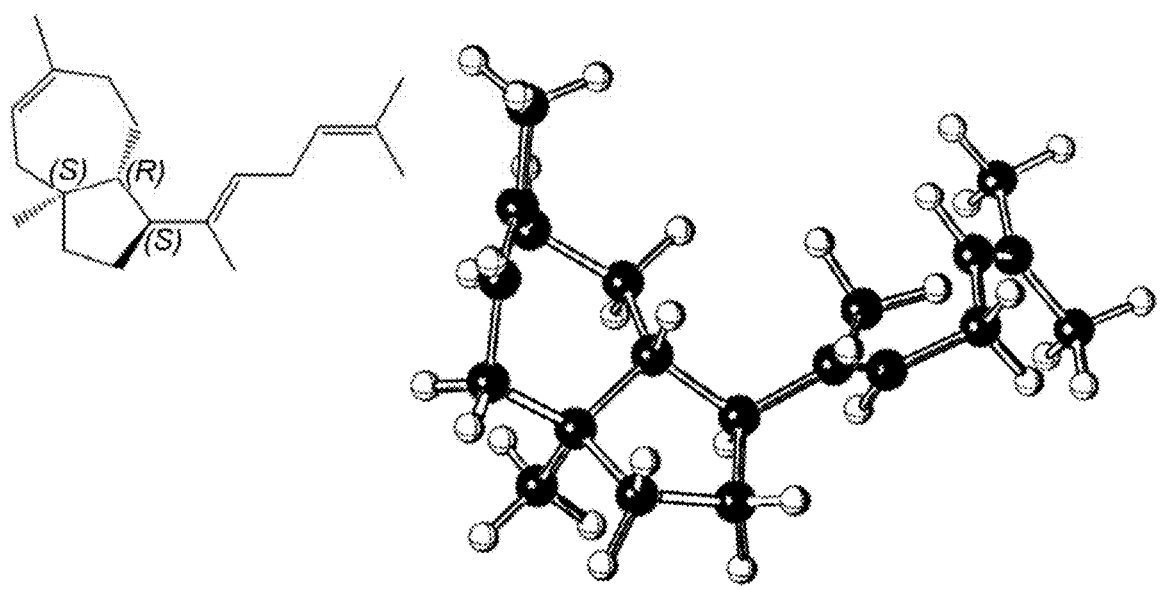
Figure 8A:
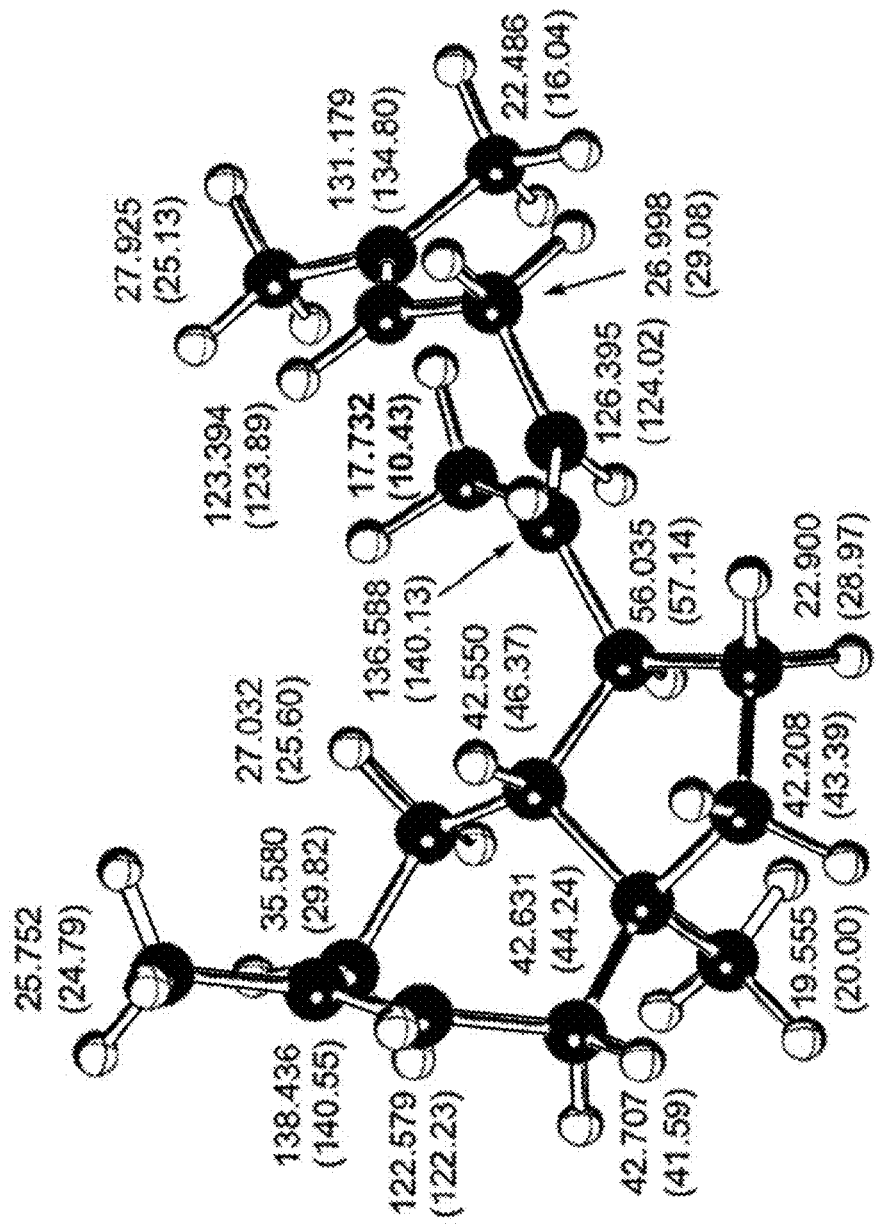
FIGS. 8A-8B NMR and quantum chemical analysis of pseudolarene. Illustrated is the structure of the PxaTPS8 reaction product verified by NMR analysis in comparison to computational chemical calculations of 1H (FIG. 8B) and 13C (FIG. 8A) chemical shifts. Experimental values are presented on top and computational data are at bottom in parentheses.
Figure 8B:
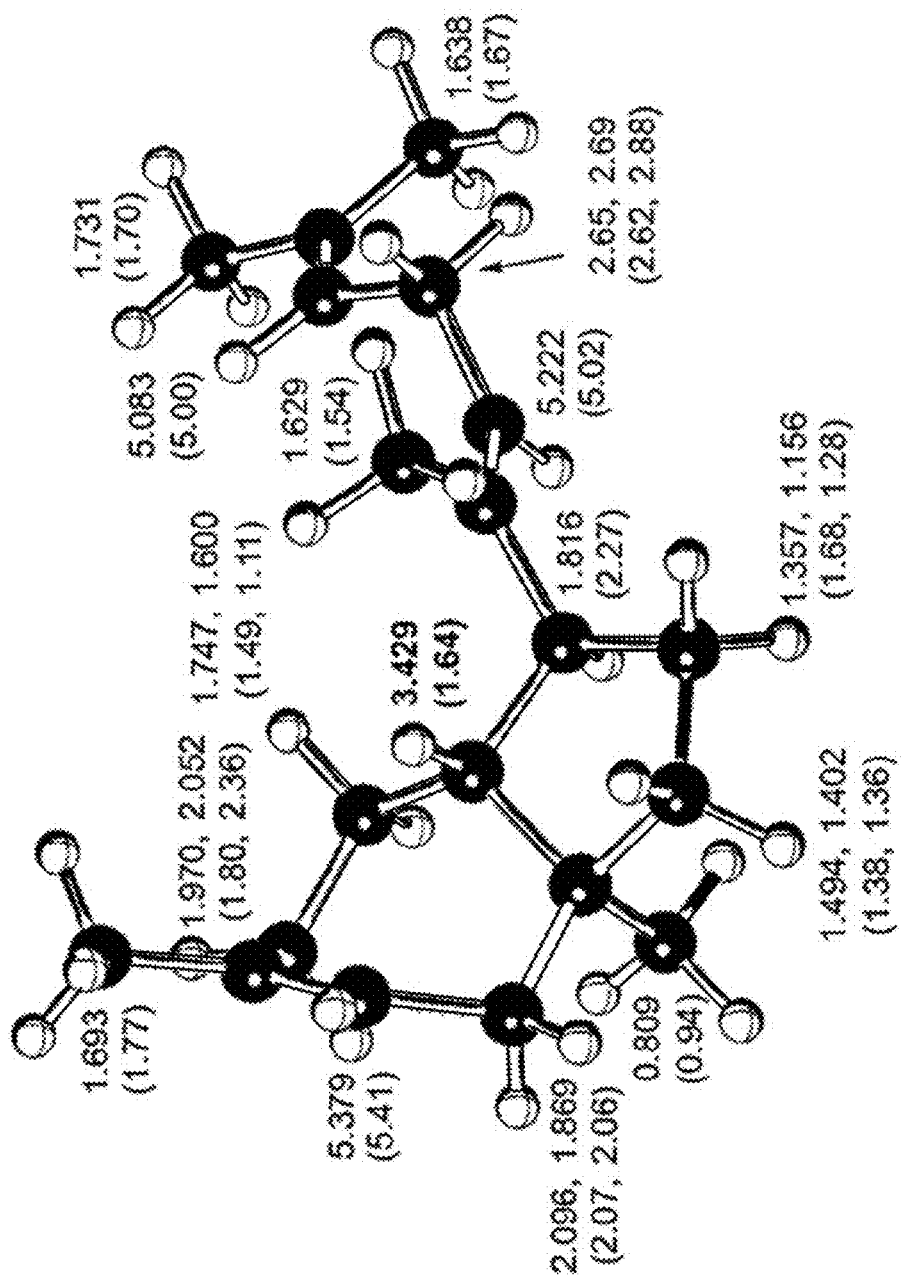

Structural elucidation of the product of PxaTPS8 as sibongilene. Using an engineered *E. coli* expression system (28) yielded sufficient amounts and purity of the PxaTPS8 product to enable 1D and 2D nuclear magnetic resonance (NMR) analysis, which identified a novel diterpene structure, termed sibongilene (FIG. 3C). In addition, we performed quantum chemical calculations of $^1$H and $^{13}$C NMR chemical shifts for several sibongilene isomers and all possible diastereomers of each (29,30) (48 structures total; FIG. 8). Mean absolute deviations (MAD) from experimental $^1$H and $^{13}$C NMR data well within accepted ranges for correct structural assignments (30) were found for the isomer of sibongilene shown in FIG. 3C (as low as 0.24 ppm for $^1$H and 2.7 ppm for $^{13}$C). To further verify our structural proposal, we performed DP4 statistical analyses (31) of computed and experimental NMR data, which indicated a >95% probability (combined $^1$H and $^{13}$C) for the depicted isomer to be correct (FIG. 8). While we are confident in the structural connectivity shown, the relative stereochemical assignment remains to be confirmed, due to the highly complex conformational sampling for the various possible diastereomers of sibongilene. Further work is underway to address this issue (for sibongilene and other flexible natural products) and will be reported in due course. These studies demonstrate PxaTPS8 as a new diTPS expanding the catalytic diversity of the enzyme family, due to its capacity for transforming GGPP into a 5,7-trans-fused bicyclic scaffold that represents the characteristic core structure of pseudolaric acids (5).

Figure 4C:
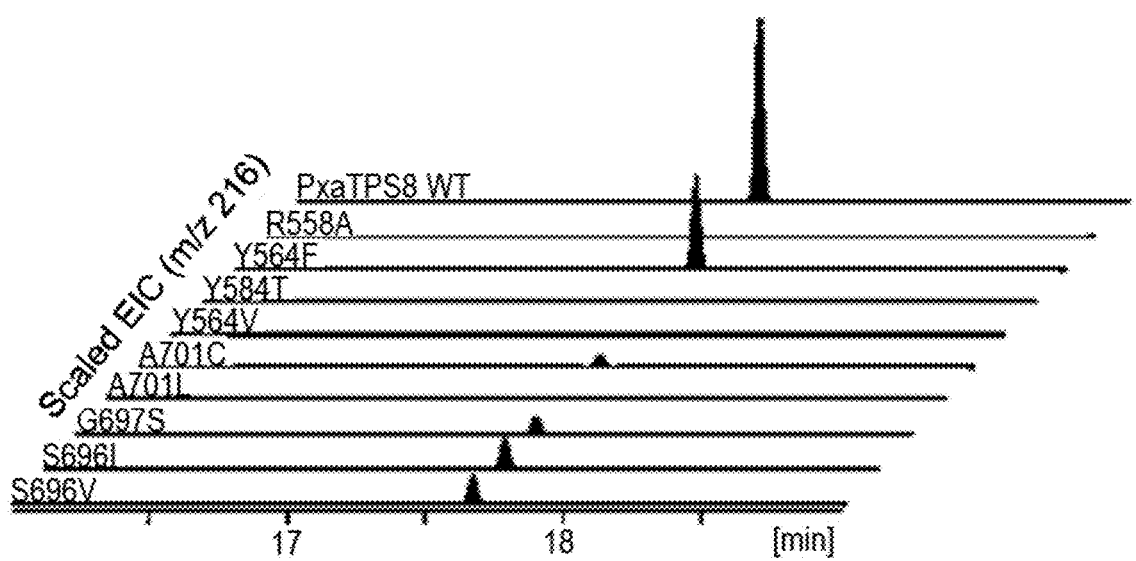
Figure 9:
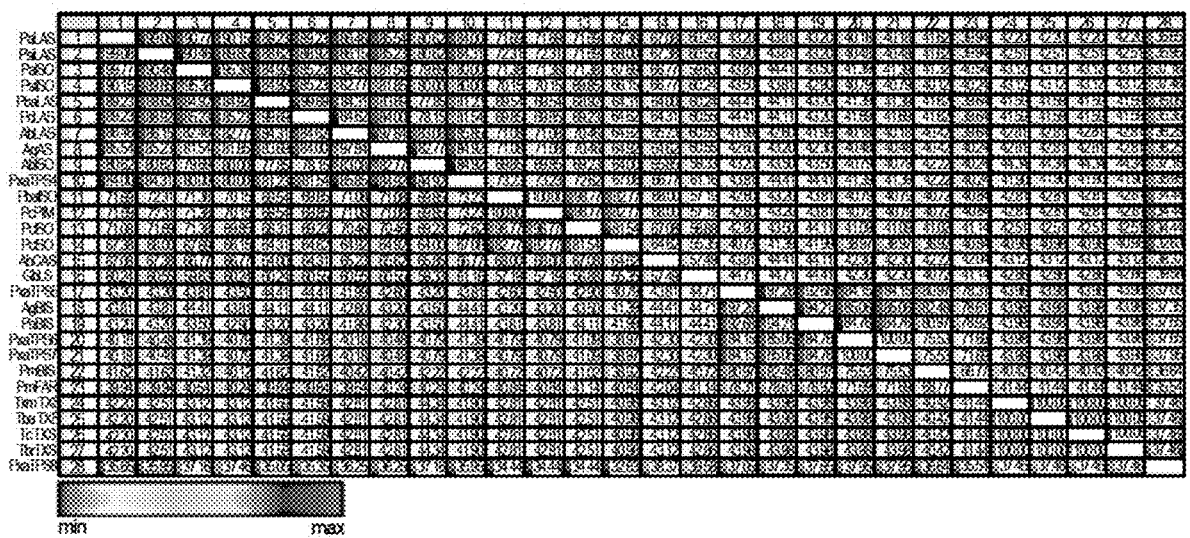
FIG. 9. Protein sequence similarity matrix of the class I active site of known gymnosperm diTPS and BIS enzymes. The class I active site is here defined as spanning from the start of helix A to the C-terminus, residues 520-846. Similarity is given in % sequence identity.

Active site determinants of PxaTPS8 function. We conducted homology modeling of PxaTPS8 based on the crystal structure of grand fir α-BIS (AgBIS) (24) and molecular docking of GGPP into the class I active site cavity to probe catalytic residues that determine the enzyme's unique activity (FIG. 4). As common features, residues of the $Mg^{2+}$-coordinating DDxxD and NSE/DTE motifs and three arginines (R558, R560, R736) previously shown as essential for substrate binding and catalysis in AgBIS and other class I TPSs are conserved in PxaTPS8. Consistently, alanine substitution of R558 abolished catalytic activity (FIG. 4). However, the low level of overall protein sequence identity of 32-38% between the class I active sites of PxaTPS8 and previously characterized gymnosperm TPSs illustrated a large degree of evolutionary divergence (FIG. 9). Notably, this included substitutions at active site positions known to impact class I TPS product specificity (24-26) (FIG. 4). Specifically, PxaTPS8 A701 located at the hinge region on helix G, and Y564 positioned at the back of the active site cavity in direct proximity to the hydrocarbon tail of the GGPP substrate appeared to be unique compared to known gymnosperm TPSs (FIG. 4). In addition, S696 and G697 are located at the hinge region, which has been highlighted as a 'hot spot' for directing product outcome in gymnosperms TPSs (24-26). Substitution of PxaTPS8 S696, G697 and A701 for different functional residues prominent in other gymnosperm TPSs led to a decrease (S696I, S696V, G697S and Ala701C) or complete loss (A701L) of activity (FIG. 4). None of the mutations resulted in changes in product or substrate specificity. In addition, substitution of Y564 for Thr, Val resulted in a loss of function, while exchange to Phe merely entailed a modest decrease in activity. This illustrates the importance of the aromatic ring in controlling sibongilene formation, likely via carbocation stabilizing to enable alkyl migration prior to deprotonation of the carbocation. These results support a function of S696, G697, A701 and Y564 in PxaTPS8 catalysis.

Figure 5A:
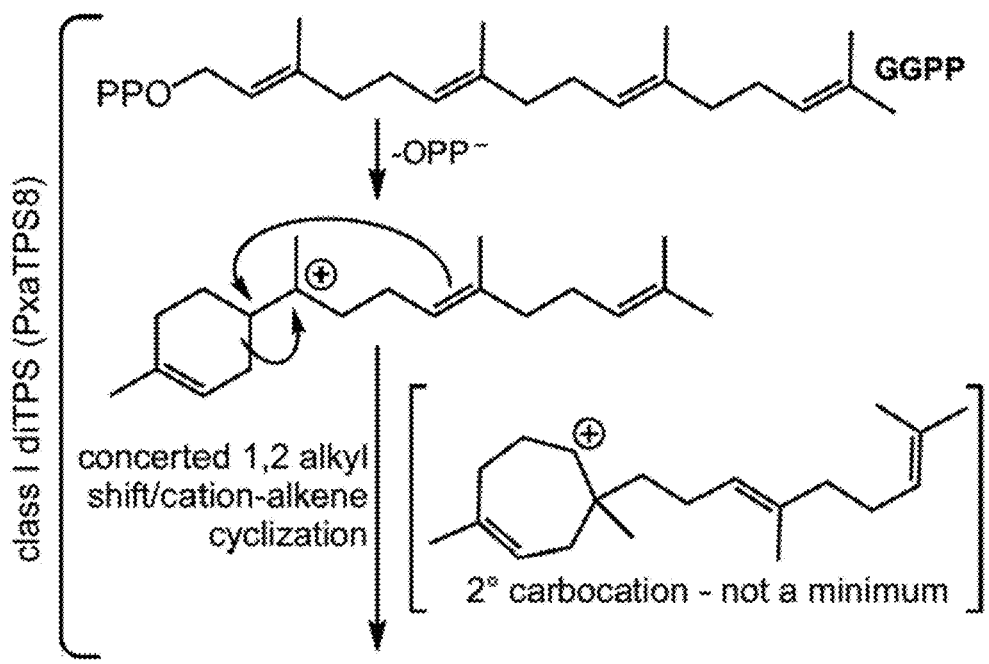
FIGS. 5A-5B Proposed mechanism of the PxaTPS8-catalyzed reaction based on quantum chemical calculations. After cleavage of the diphosphate group of GGPP, the initial carbocation (FIG. 5A) forms via 1,6-cyclization. Single step 1,2-alkyl shift and 6,10-cyclization afford a second carbocation (FIG. 5B) with the characteristic 5,7-fused bicyclic structure. Deprotonation of (FIG. 5B) yields sibongilene.
Figure 5B:
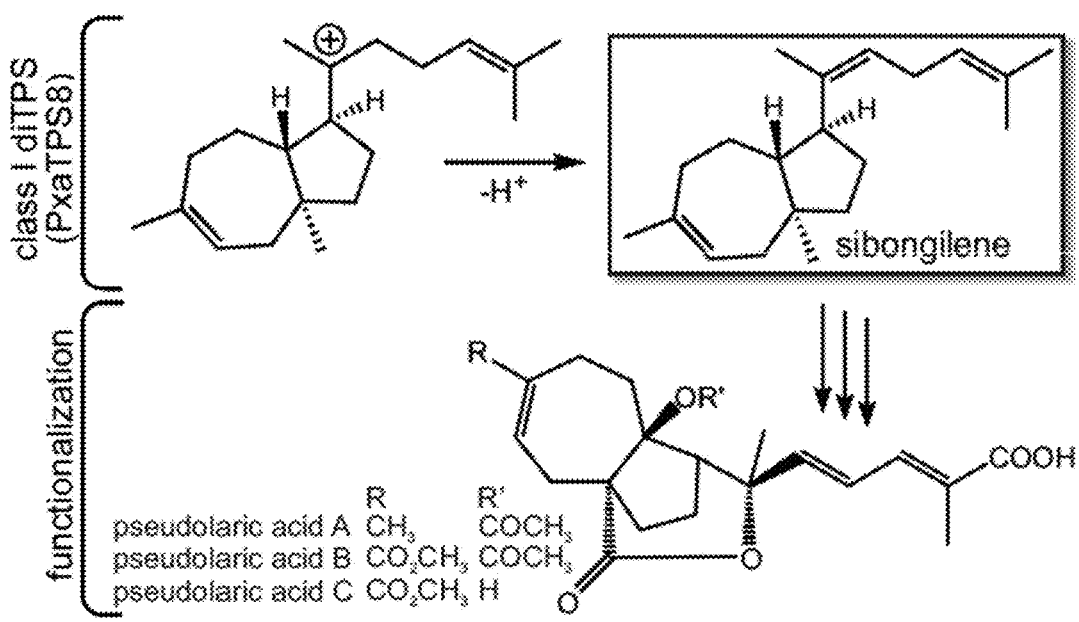

Quantum chemical calculations reveal a unique reaction mechanism in sibongilene formation. We used quantum chemical calculations (mPW1PW91/6-31+G(d,p)//B3LYP/6-31+G(d,p); (30,32) to assess the viability of carbocation cyclization and rearrangement mechanisms for sibongilene formation (see FIG. 8 for computed geometries and additional details; a single diastereomer is discussed here, but similar results were found for other diastereomers). According to these calculations, the first carbocation intermediate (A) results from initial 1,6-cyclization (FIG. 5). The subsequent 1,2-alkyl shift and 6,10-cyclization occur in a single step (33) to form a carbocation (B) with the characteristic 5,7-fused bicyclic scaffold. The product of this step has a calculated energy 3.4 kcal/mol higher than A, and is formed with an activation energy of 13.6 kcal/mol. Deprotonation of B would form the final product (sibongilene).

Figure 10:
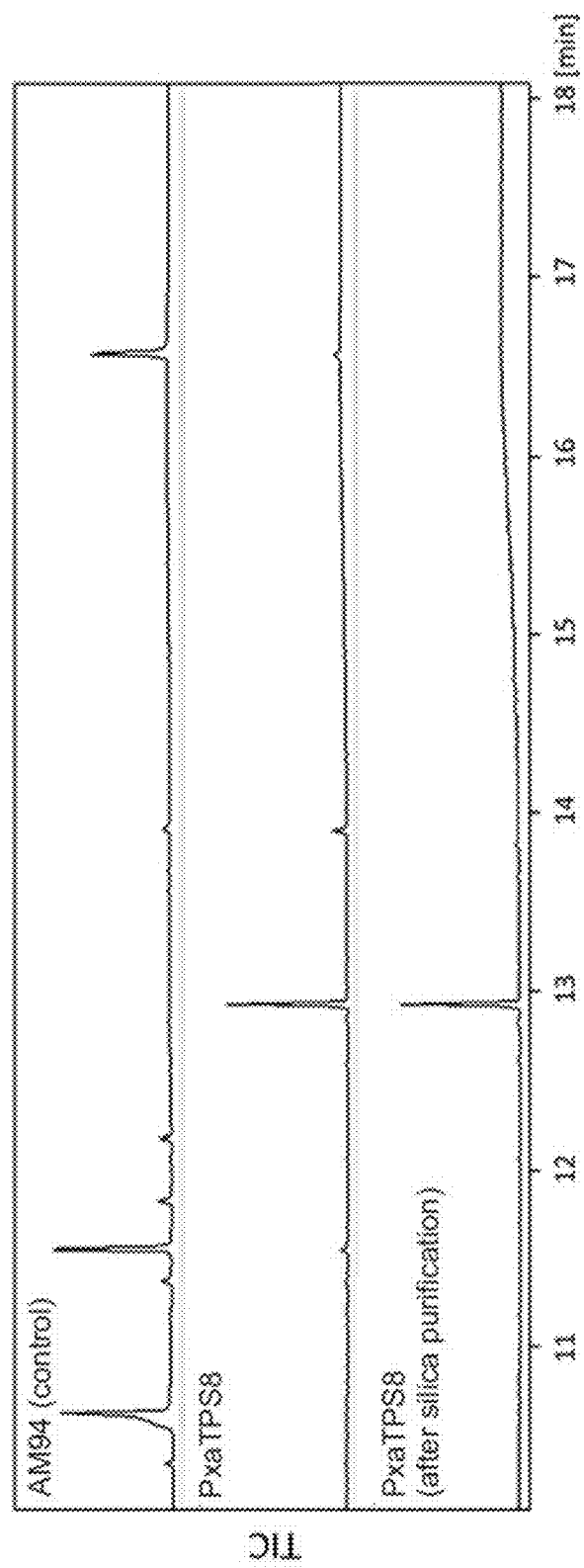
FIG. 10. Sibongilene formation in engineered yeast. Shown are GC/MS total ion chromatograms (TIC) of the PxaTPS8 production after co-expression with the yeast GGPP synthase (BTS1) in the engineered yeast (*S. cerevisiae*) strain AM94. Sibongilene was purified on silica matrix.

Formation of sibongilene in engineered yeast To develop a proof-of-concept production platform for sibongilene, we co-transformed PxaTPS8 with the yeast (*Saccharomyces cerevisiae*) GGPP synthase BTS1 (34) in the engineered yeast strain AM94 that provides elevated terpene precursor yield (35). Sibongilene was abundant solely in cell pellets after induction with galactose for 41 h, yielding a product amount of 1 mg per L culture (FIG. 10). Dephosphorylated GGPP and squalene as major by-products after diethyl ether extraction could be readily removed by simple chromatography on silica matrix to afford sibongilene in greater than 90% purity. These findings outline a promising foundation for a microbial production system for sibongilene to enable efficient discovery of downstream pathway components and related diterpene structures.

DISCUSSION

The vast chemical space of diterpene natural products, which originate from the natural variation of diTPS enzymes, provides a rich repertoire of known and potentially new pharmaceutical lead compounds. Exploring diterpene chemical diversity continues to be important as drug discovery of recent decades has been falling short of meeting the demand for new and improved therapies (36). Currently, only a few plant-derived diterpene pharmaceuticals, such as taxol and forskolin, are available at industrially relevant scale (2,4), due to the often low abundance of diterpenes in the natural source material or uneconomic chemical synthesis.

Pseudolaric acids from the traditional Chinese medicinal tree golden larch have been recognized for their chemotherapeutic potential and prevention of multidrug resistance (6-9). The discovery of golden larch PxaTPS8 presents a unique new catalyst among the diTPS portfolio with applications for biotechnological production of pseudolaric acids.

Biochemical and quantum chemical mechanistic insights into the PxaTPS8-facilitated formation of sibongilene substantially expand our knowledge of the mechanistic and evolutionary underpinnings of diterpene chemical diversity. The conversion of GGPP to sibongilene (FIG. 5) exemplifies an exceedingly short mechanism that underscores nature's ability to take advantage of inherent carbocation reactivity to generate a structurally complex product without much worry of diversion to other products that may arise if more discrete intermediates were involved (32,33,37). This hypothesis is further supported by the observation that substitution of select active site residues known to alter product specificity in other diTPSs only entailed a reduced activity but no functional change in PxaTPS8 (FIG. 5).

Prior to this work, knowledge of secondary diterpene metabolism in gymnosperms included the bifunctional class I/II diTPSs involved in the biosynthesis of labdane diterpenes and derived diterpene resin acids of conifer chemical defense (25). In addition, only a few monofunctional class I diTPSs involved in diterpene resin acid biosynthesis in pine and taxane formation in species of yew had been described (2,4; FIG. 6). All of these represent 3-domain enzymes of the TPS-d3 clade (FIG. 2). Surprisingly, PxaTPS8, which marks a diTPS catalyzing a new reaction mechanism en route to a unique diterpene, sibongilene, was identified as the first 3-domain diTPS at the base of the TPS-dl clade (FIGS. 2 & 3). The 3-domain structure of PxaTPS8 suggests a common origin with BIS enzymes. It appears that BIS-like genes in golden larch, of which there are at least four different members, may have undergone more substantial evolution with regard to gene number and functions compared to the corresponding, apparently single copy BIS genes in other gymnosperm species (20,27,38,39). And this diversification may have resulted in the unique pseudolaric acid biosynthesis in the golden larch tree as the sole species of its genus. The sibongilene scaffold may be unique to diterpenes of golden larch, but structurally similar sphenolobane and tormesane diterpenes have been described in liverworts of the genus *Anastrophylum* (40) and the eudicot *Halimium viscosum* (Cristaceae; 41). However, diTPSs of these species are not known.

Considering the low abundance of PAB in the roots of golden larch (11), metabolic engineering of PxaTPS8 into a microbial or plant host paves the way to sibongilene production for semi-synthesis of PAB and related compounds.

Such a recombinant system also provides a superb platform for accelerating the discovery of downstream enzymes of PBA biosynthesis.

REFERENCES

1. De Luca V, Salim V, Atsumi S M, Yu F (2012) Mining the biodiversity of plants: a revolution in the making. *Science* 336(6089):1658-61.
2. Zerbe P, Bohlmann J (2015) Plant diterpene synthases: exploring modularity and metabolic diversity for bioengineering. *Trends Biotechnol* 33(7):419-28
3. Tholl D (2015) Biosynthesis and biological functions of terpenoids in plants. *Adv Biochem Eng Biotechnol* 148: 63-10.
4. Bohlmann J, Keeling C I (2008) Terpenoid biomaterials. *Plant J* 54(4):656-69.
5. Chiu P, Leung L T, Ko B C B (2010) Pseudolaric acids: isolation, bioactivity and synthetic studies. *Nat Prod Rep* 27(7):1066-83.
6. Wong V K W et al. (2005) Pseudolaric acid B, a novel microtubule-destabilizing agent that circumvents multidrug resistance phenotype and exhibits antitumor activity in vivo. *Clin Cancer Res Off J Am Assoc Cancer Res* 11(16):6002-11.
7. Li M, Hong L (2015) Pseudolaric acid B exerts antitumor activity via suppression of the Akt signaling pathway in HeLa cervical cancer cells. *Mol Med Rep* 12(2):2021-6.
8. Sun Q, Li Y (2014) The inhibitory effect of pseudolaric acid B on gastric cancer and multidrug resistance via Cox-2/PKC-α/P-gp pathway. *PloS One* 9(9):e107830.
9. Sarkar T et al. (2012) Interaction of pseudolaric acid B with the colchicine site of tubulin. *Biochem Pharmacol* 84(4):444-50.
10. Trost B M, Waser J, Meyer A (2008) Total synthesis of (−)-pseudolaric acid B. *J Am Chem Soc* 130(48):16424-34.
11. Zerbe P et al. (2013) Gene discovery of modular diterpene metabolism in nonmodel systems. *Plant Physiol* 162(2):1073-91.
12. Chen F, Tholl D, Bohlmann J, Pichersky E (2011) The family of terpene synthases in plants: a mid-size family of genes for specialized metabolism that is highly diversified throughout the kingdom. *Plant J* 66(1):212-29.
13. Peters R J (2010) Two rings in them all: the labdane-related diterpenoids. *Nat Prod Rep* 27(11):1521-30.
14. Zhou K et al. (2012) Insights into diterpene cyclization from structure of bifunctional abietadiene synthase from *Abies grandis*. *J Biol Chem* 287(9):6840-50.
15. Köksal M, Jin Y, Coates R M, Croteau R, Christianson D W (2011) Taxadiene synthase structure and evolution of modular architecture in terpene biosynthesis. *Nature* 469 (7328):116-20.
16. Gao Y, Honzatko R B, Peters R J (2012) Terpenoid synthase structures: a so far incomplete view of complex catalysis. *Nat Prod Rep* 29(10):1153-75.
17. Schepmann H G, Pang J, Matsuda S P (2001) Cloning and characterization of *Ginkgo biloba* levopimaradiene synthase which catalyzes the first committed step in ginkgolide biosynthesis. *Arch Biochem Biophys* 392(2): 263-9.
18. Zerbe P et al. (2012) Bifunctional cis-abienol synthase from *Abies balsamea* discovered by transcriptome sequencing and its implications for diterpenoid fragrance production. *J Biol Chem* 287(15):12121-31.
19. Peters R J et al. (2000) Abietadiene synthase from grand fir (*Abies grandis*): characterization and mechanism of action of the "pseudomature" recombinant enzyme. *Biochemistry* 39(50):15592-602.
20. Martin D M, Faldt J, Bohlmann J (2004) Functional characterization of nine Norway Spruce TPS genes and evolution of gymnosperm terpene synthases of the TPS-d subfamily. *Plant Physiol* 135 (4):1908-27.
21. Keeling C I, Madilao L L, Zerbe P, Dullat H K, Bohlmann J (2011) The primary diterpene synthase products of *Picea abies* levopimaradiene/abietadiene synthase (PaLAS) are epimers of a thermally unstable diterpenol. *J Biol Chem* 286(24):21145-53.
22. Hall D E et al. (2013) Evolution of conifer diterpene synthases: diterpene resin acid biosynthesis in lodgepole pine and jack pine involves monofunctional and bifunctional diterpene synthases. *Plant Physiol* 161(2):600-16.
23. Wildung M R, Croteau R (1996) A cDNA clone for taxadiene synthase, the diterpene cyclase that catalyzes the committed step of taxol biosynthesis. *J Biol Chem* 271(16):9201-4.
24. McAndrew R P et al. (2011) Structure of a three-domain sesquiterpene synthase: a prospective target for advanced biofuels production. *Structure* 19(12):1876-84.
25. Keeling C I, Weisshaar S, Lin R P C, Bohlmann J (2008) Functional plasticity of paralogous diterpene synthases involved in conifer defense. *Proc Natl Acad Sci* 105(3): 1085-90.
26. Peters R J, Croteau R B (2002) Abietadiene synthase catalysis: mutational analysis of a prenyl diphosphate ionization-initiated cyclization and rearrangement. *Proc Natl Acad Sci* 99(2):580-4.
27. Bohlmann J, Crock J, Jetter R, Croteau R (1998) Terpenoid-based defenses in conifers: cDNA cloning, characterization, and functional expression of wound-inducible (E)-☐-bisabolene synthase from grand fir (*Abies grandis*). *Proc Natl Acad Sci* 95(12):6756-61.
28. Morrone D et al. (2010) Increasing diterpene yield with a modular metabolic engineering system in *E. coli*: comparison of MEV and MEP isoprenoid precursor pathway engineering. *Appl Microbiol Biotechnol* 85(6):1893-906.
29. Vaughan M M et al. (2013) Formation of the unusual semivolatile diterpene rhizathalene by the *Arabidopsis* class I terpene synthase TPS08 in the root stele is involved in defense against belowground herbivory. *The Plant Cell* 25:1108-25.
30. Lodewyk M W, Siebert M R, Tantillo D J (2012) Computational prediction of $^1$H and $^{13}$C chemical shifts: A useful tool for natural product, mechanistic, and synthetic organic chemistry. *Chem Rev* 112(3): 1839-62.
31. Smith S G, Goodman J M (2010) Assigning stereochemistry to single diastereomers by GIAO NMR calculation: The DP4 probability. *J Am Chem Soc* 132:12946-59.
32. Tantillo D J (2013) Walking in the woods with quantum chemistry-applications of quantum chemical calculations in natural products research. *Nat Prod Rep* 30(8):1079-86.
33. Tantillo D J (2010) The carbocation continuum in terpene biosynthesis—where are the secondary cations? *Chem Soc Rev* 39(8):2847-54.
34. Ro D K, Bohlmann J (2006) Diterpene resin acid biosynthesis in loblolly pine (*Pinus taeda*): functional characterization of abietadiene-levopimaradiene synthase (PtTPS-LAS) cDNA and subcellular targeting of PtTPS-LAS and abietadienol/abietadienal oxidase (PtAO, CYP720B1). *Phytochemistry* 67(15):1572-8.
35. Ignea C et al. (2015) Efficient diterpene production in yeast by engineering Erg20p into a geranylgeranyl diphosphate synthase. *Metab Eng* 27:65-7.

36. Scannell J W, Blanckley A, Boldon H, Warrington B (2012) Diagnosing the decline in pharmaceutical R&D efficiency. *Nat Rev Drug Discov* 11:191-200.
37. Tantillo D J. Biosynthesis via carbocations: theoretical studies on terpene formation. *Nat Prod Rep* 28(6):1035-53.
38. Parveen I et al. (2015) Investigating sesquiterpene biosynthesis in *Ginkgo biloba*: molecular cloning and functional characterization of (E,E)-farnesol and α-bisabolene synthases. *Plant Mol Biol* 89(4-5): 451-62.
39. Huber D P et al. (2005) Characterization of four terpene synthase cDNAs from methyl jasmonate-induced Douglas-fir, *Pseudotsuga menziesii*. *Phytochemistry* 66(12): 1427-39.
40. Buchanan M S, Connolly J D, Rycroft D S (1996) Sphenolobane diterpenoids of the liverwort *Anastrophyllum donnianum*. *Phytochemistry* 43(6): 1297-301.
41. Urones J G, Marcos I S, Garrido M D (1990) Tormesane derivatives of *Halimium viscosum*. *Phytochemistry* 29(10): 3243-46.
42. Voinnet O, Rivas S, Mestre P, Baulcombe D (2003) An enhanced transient expression system in plants based on suppression of gene silencing by the p19 protein of tomato bushy stunt virus. *Plant J* 33(5):949-56.
43. Frisch M J et al. (2009) Gaussian 09, Revision B.01, Gaussian, Inc., Wallingford Conn.
44. Becke A D (1993) Density-functional thermochemistry. III. The role of exact exchange. *J Chem Phys* 98:5648.
45. Becke A D (1993) A new mixing of Hartree-Fock and local density-functional theories. *J Chem Phys* 98:1372.
46. Lee C, Yang W, Parr R G (1988) Development of the Colic-Salvetti correlation-energy formula into a functional of the electron density. *Phys Rev* 37(2):785-9.
47. Tirado-Rives J, Jorgensen W L (2008) Performance of B3LYP density functional methods for a large set of organic molecules. *J Chem Theory Comput* 4:297-306.
48. Shao et al. (2006) Advances in methods and algorithms in a modern quantum chemistry program package. *Phys Chem Chem Phys* 8:3172-91.
49. Halgren T A (1996) Merck molecular force field. I. Basis, form, scope, parameterization, and performance of MMFF94. *J Comp Chem* 17:490-519.
50. Marenich A V, Cramer C J, Truhlar D J (2009) Universal solvation model based on solute electron density and on a continuum model of the solvent defined by the bulk dielectric constant and atomic surface tensions. *J Phys Chem B* 113:6378-96.
51. Matsuda S P T, Wilson W K, Xiong Q (2006) Mechanistic insights into triterpene synthesis from quantum mechanical calculations. Detection of systematic errors in B3LYP cyclization energies. *Org Biomol Chem* 4:530-43.
52. Maeda S et al. (2015) Intrinsic reaction coordinate: calculation, bifurcation, and automated search. *Int J Quantum Chem* 115:258-69.
53. Potter K C et al. (2016) Blocking Deprotonation with Retention of Aromaticity in a Plant ent-Copalyl Diphosphate Synthase Leads to Product Rearrangement. *Angew Chem Int Ed Engl* 55(2):634-8.
54. Talavera G, Castresana J (2007) Improvement of phylogenies after removing divergent and ambiguously aligned blocks from protein sequence alignments. *Syst Biol* 56(4):564-77.
55. Guindon S et al. (2009) Estimating maximum likelihood phylogenies with PhyML. *Methods Mol Biol* 537:113-37.
56. Thomsen R, Christensen M H (2006) MolDock: a new technique for high-accuracy molecular docking. *J Med Chem* 49(11):3315-21.

What is claimed is:

1. An isolated nucleic acid molecule, comprising a promoter operably linked to a sequence of nucleotides encoding a diterpene synthase polypeptide at least 95% identical to SEQ ID NO:1 or an active fragment thereof wherein the diterpene synthase polypeptide catalyzes the formation of sibongilene from geranylgeranyl diphosphate (GGPP), and wherein the promoter is not native to the sequence of nucleotides.

2. The isolated nucleic acid of claim 1, wherein the diterpene synthase polypeptide comprises SEQ ID NO:1.

3. A vector comprising the isolated nucleic acid of claim 1.

4. A host cell comprising nucleic acid molecule; comprising a sequence of nucleotides encoding a diterpene synthase polypeptide at least 95% identical to SEQ ID NO:1 or an active fragment thereof, wherein the diterpene synthase polypeptide catalyzes the formation of sibongilene from geranylgeranyl diphosphate (GGPP), wherein the encoded diterpene synthase polypeptide is heterologous to the host cell.

5. The host cell of claim 4 that is a prokaryotic host cell.

6. The host cell of claim 4 that is a eukaryotic host cell.

7. The host cell of claim 5 that is an *E. coli* cell.

8. The host cell of claim 6, wherein the host cell is selected from the group consisting of a fungal, plant, insect, and amphibian host cell.

9. The host cell of claim 6, wherein the host cell is an animal cell.

10. The host cell of claim 6, wherein the host cell is a yeast cell.

11. The host cell of claim 4, wherein the host cell produces a 7,5-fused bicyclic diterpene.

12. The host cell of claim 11, wherein the host cell produces sibongilene.

13. A method of producing a 7,5-fused bicyclic diterpene, comprising: i) contacting (E,E,E)-geranylgeranyl diphosphate (GGPP) with the diterpene synthase polypeptide of claim 1 under conditions effective to produce the cis-7,5-fused bicyclic diterpene, wherein: contacting is effected with an isolated diterpene synthase polypeptide, or contacting is effected in a host cell comprising the nucleic acid molecule, and the nucleic acid molecule is heterologous to the host cell; and ii) optionally, isolating the 7,5-fused bicyclic diterpene produced in step i).

14. The method of claim 13, wherein the 7,5-fused bicyclic diterpene is sibongilene.

15. The method of claim 13, wherein the method further comprises isolating the 7,5-fused bicyclic diterpene.

16. The method of claim 13, wherein the method further comprises converting the 7,5-fused bicyclic diterpene to a pseudolaric acid.

17. The method of claim 13, wherein the method further comprises converting the 7,5-fused bicyclic diterpene to pseudolaric acid B.

18. The method of claim 17, wherein the method further comprises isolating the pseudolaric acid B.

19. The host cell of claim 4, wherein the diterpene synthase polypeptide comprises SEQ ID NO:1.

20. The method of claim 13, wherein the diterpene synthase polypeptide comprises SEQ ID NO:1.

\* \* \* \* \*